(12) United States Patent
Nuckolls et al.

(10) Patent No.: US 7,928,432 B2
(45) Date of Patent: Apr. 19, 2011

(54) SENSING DEVICES FROM MOLECULAR ELECTRONIC DEVICES

(75) Inventors: Colin Nuckolls, New York, NY (US); Xuefeng Guo, New York, NY (US); Philip Kim, New York, NY (US)

(73) Assignee: The Trustees Of Columbia University In The City Of New York, New York, NY (US)

( * ) Notice: Subject to any disclaimer, the term of this patent is extended or adjusted under 35 U.S.C. 154(b) by 131 days.

(21) Appl. No.: 12/139,218

(22) Filed: Jun. 13, 2008

(65) Prior Publication Data

US 2009/0017571 A1    Jan. 15, 2009

Related U.S. Application Data

(63) Continuation of application No. PCT/US2006/061568, filed on Dec. 4, 2006.

(60) Provisional application No. 60/750,994, filed on Dec. 15, 2005, provisional application No. 60/750,993, filed on Dec. 15, 2005, provisional application No. 60/762,095, filed on Jan. 25, 2006, provisional application No. 60/814,604, filed on Jun. 16, 2006.

(51) Int. Cl.
*H01L 35/24* (2006.01)

(52) U.S. Cl. ............... 257/40; 257/48; 257/E39.001; 257/E51.038; 977/701; 977/721

(58) Field of Classification Search .............. 257/40, 257/48, E51.038, E39; 977/701, 721
See application file for complete search history.

(56) References Cited

U.S. PATENT DOCUMENTS

| | | | |
|---|---|---|---|
| 6,723,394 B1 | 4/2004 | Sirringhaus et al. | |
| 2004/0009114 A1* | 1/2004 | Margrave et al. | 423/447.1 |
| 2005/0019791 A1* | 1/2005 | Jung et al. | 435/6 |
| 2005/0176228 A1 | 8/2005 | Fonash et al. | |
| 2006/0038299 A1* | 2/2006 | Hirakata et al. | 257/773 |

OTHER PUBLICATIONS

Besteman et al. "Enzyme-coated carbon nanotubes as single molecule biosensors" 2003, *Nano Ltrs.*, 3(6): 727-30.
Huang et al. "Controlled Growth of Single-Walled Carbon Nanotubes from an Ordered Mesoporous Silica Template" 2003, *Nano Ltrs.*, 3(3):299-303.
Huang et al. "Long and Oriented Single-Walled Carbon Nanotubes Grown by Ethanol Chemical Vapor Deposition" 2004, *J. Phys. Chem. B*, 108(42):16451-6.
Huffman et al "Formylation of Amines" 1958, *J. Org. Chem.*, 23(5):727-9.

(Continued)

*Primary Examiner* — Wai-Sing Louie
(74) *Attorney, Agent, or Firm* — Baker Botts LLP

(57) ABSTRACT

The present invention generally relates to the fabrication of molecular electronics devices from molecular wires and Single Wall Nanotubes (SWNT). In one embodiment, the cutting of a SWNT is achieved by opening a window of small width by lithography patterning of a protective layer on top of the SWNT, followed by applying an oxygen plasma to the exposed SWNT portion. In another embodiment, the gap of a cut SWNT is reconnected by one or more difunctional molecules having appropriate lengths reacting to the functional groups on the cut SWNT ends to form covalent bonds. In another embodiment, the gap of a cut SWNT gap is filled with a self-assembled monolayer from derivatives of novel contorted hexabenzocoranenes. In yet another embodiment, a device based on molecular wire reconnecting a cut SWNT is used as a sensor to detect a biological binding event.

19 Claims, 21 Drawing Sheets

OTHER PUBLICATIONS

Klare et al. "Chemical reactions with upright monolayers of cruciform pi-systems" 2004, *Langmuir*, 20(23):10068-72.

Lustig et al. "Lithographically cut single-walled carbon nanotubes: controlling length distribution and introducing end-group functionality" 2003, *Nano Ltrs.*, 3(8):1007-12.

Mao et al. "Synthesis and structure-property relationships of regioirregular poly(3-hexylthiophenes)" 1993, *Macromolecules*, 26:1163-9.

Melissarie et al. "A Simple and Economical Synthetic Route to p-Ethynylaniline and Ethynyl-Terminated Substrates" 1994, *J. Org. Chem.*, 59(19):5818-21.

Sadighi et al. "Palladium-Catalyzed Synthesis of Monodisperse, Controlled-Length, and Functionalized Oligoanilines" 1998, *J. Am. Chem. Soc.*, 120(20):4960-76.

Soncini et al. "Perimeter Effects on Ring Currents in Polycyclic Aromatic Hydrocarbons: Circumcoronene and Two Hexabenzocoronenes" 2003, *Chem. Eur. J.*, 9,(13):2974-81.

Toshiki et al. "Phenyl-substituted 2,2:6,2-terpyridine as a new series of fluorescent compounds—their photophysical properties and fluorescence tuning" 2001, *J. Chem. Soc., Perkin Trans. 2*, 7:1045-50.

Wu et al. "Convergent Synthetic Routes to Orthogonally Fused Conjugated Oligomers Directed toward Molecular Scale Electronic Device Applications" 1996, *J. Org. Chem.*, 61(20):6906-21.

Xiao et al. "Molecular wires from contorted aromatic compounds" 2005, *Angew. Chem. Int. Ed.*, 44:7390-4.

Yun et al. "Electrochemically grown wires for individually addressable sensor arrays" 2004, *Nano ltrs.*, 4(3):419-22.

Dai et al., "Sensors and sensor arrays based on conjugated polymers and carbon nanotubes," Pure Appl. Chem. 2002, vol. 74, No. 9, pp. 1753-1772.

Austin et al. "Fabrication of 5 nm linewidth and 14 nm pitch features by nanoimprint lithography," Applied Physics Letters, Jun. 28, 2004, vol. 84, No. 26, pp. 5299-5301.

Qi et al., "Miniature organic transistors with carbon nanotubes as quasi-one-dimensional electrodes," JACS Communications, Sep. 1, 2004, vol. 126, pp. 11774-11775.

U.S. Appl. No. 11/566,437, filed Dec. 4, 2006.

U.S. Appl. No. 12/139,207, filed Jun. 13, 2008.

U.S. Appl. No. 11/566,437, Restriction Requirement—Dec. 26, 2008.

U.S. Appl. No. 11/566,437, Response to Restriction Requirement—Jan. 15, 2009.

U.S. Appl. No. 11/566,437, Non-Final Office Action—Mar. 16, 2009.

U.S. Appl. No. 11/566,437, Response to Non-Final Office Action—May 29, 2009.

U.S. Appl. No. 11/566,437, Final Office Action—Sep. 3, 2009.

Soncini et al., Perimeter Effects on Ring Currents in Polycyclic Aromatic Hydrocarbons: Circumcoronene and Two Hexabenzocoronenes, Jul. 7, 2003, Chemistry European Journal, vol. 9, No. 13, pp. 2974-2981.

\* cited by examiner key: (a) Lawesson's reagent; (b) THF, then PPh₃; (c) KMnO₄;
(d) Lawesson's reagent; (e) THF, then PPh₃; (f) hv, I₂, propylene oxide.

key: (a) hv, I₂, propylene oxide.

R=4-dodecycloxybenzyl
9

R=hexyl
10

11

12 planar alignment of columns

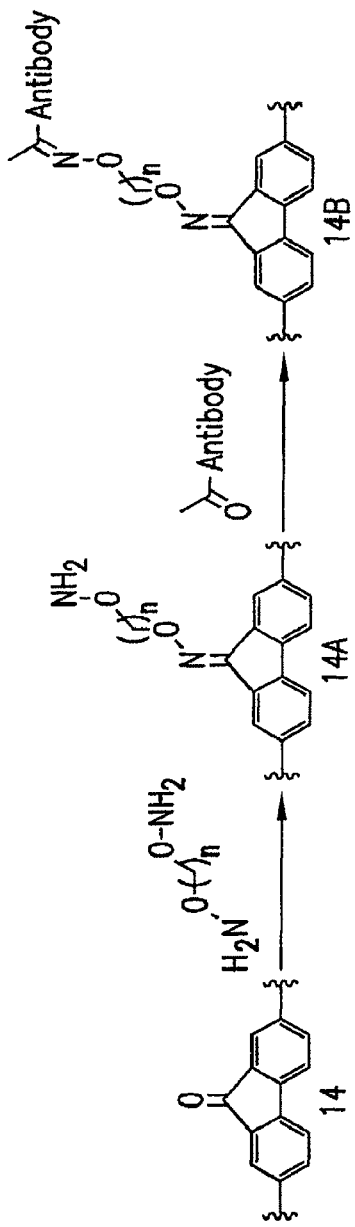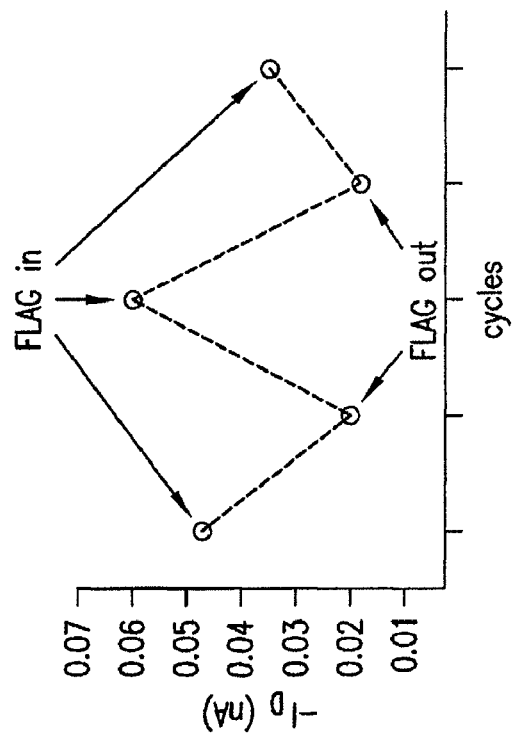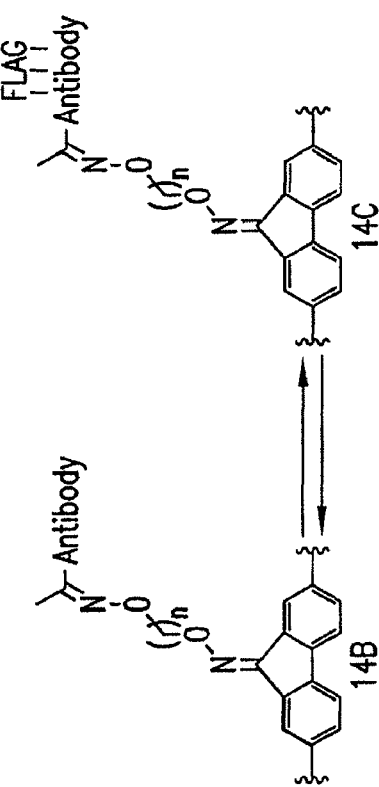
FIG. 19A
FIG. 19B
FIG. 19C

SENSING DEVICES FROM MOLECULAR ELECTRONIC DEVICES

CROSS-REFERENCE TO RELATED APPLICATIONS

This application is a continuation of International Application PCT/US2006/061568, filed Dec. 4, 2006 which claims the benefit of priority of Provisional Application Nos. 60/750,994 and 60/750,993, both filed on Dec. 15, 2005; Provisional Application No. 60/762,095, filed on Jan. 25, 2006; and Provisional Application No. 60/814,604, filed on Jun. 16, 2006, the entire contents of each are incorporated by reference herein.

STATEMENT REGARDING FEDERALLY SPONSORED RESEARCH

The invention described herein was funded in part by grants from NSF Award Number CHE-0117752 and by the New York State Office of Science, Technology, and Academic Research (NYSTAR). PK thanks the NSF CAREER (DMR-0349232) and DARPA (N00014-04-1-0591). The United States Government may have certain rights under the invention.

BACKGROUND OF THE INVENTION

1. Technical Field

The present invention relates to nanotube-based electronic devices, including devices which incorporate organic molecules.

2. Background Art

The field of molecular electronics has become one of the most exciting technology areas in recent years. Molecular electronics devices are significantly smaller, more energy efficient and less expensive to manufacture than their silicon-based counterparts. They are regarded as one of the most promising technological alternatives to overcome the inherent scaling limits of silicon devices.

A basis for molecular electronics lies in organic molecules that are capable of conducting electricity and switching between on and off states as a result of external manipulations (in a similar manner as silicon-based transistors). One way to build such a molecular electronic device is to use an organic film as an active channel between the metallic source and drain electrodes. The molecular structure and a molecule's capability of packing in some form of ordered structure are crucial to facilitate electron transport through the channel. However, the selection of appropriate molecules has proven to be a great challenge.

An alternative way to build such a device is to bridge two ends of an individual molecule directly to the source and drain electrodes. This method does not require that the molecule form any ordered structure, and will result in a circuit with much smaller channel region with extraordinary properties. However, due to the constraints of traditional lithography, the gaps between the metal electrodes are usually large compared to the size of small organic molecules, making the bridging very difficult.

One feature of the latter kind of devices is very small contact areas between the conducting molecules and the electrodes. As a result, the electron transport at the junction points between the molecular wires and metal electrodes becomes significant in the circuit characteristics. However, bonding between organic molecules and metal electrodes is difficult to accomplish, and is notoriously ill-defined even when accomplished. For example, as reported in M. A. Reed et al., Science vol. 278, p. 252 (1997); A. Salomon et al., Adv. Mater. vol. 15, p. 1881 (2003), no methods have been identified to control the type of metal-molecule bonding in the most well-studied system involving thiolated molecules on Au contacts. Moreover, as reported in H. Basch et al., Nano Lett. vol. 5, p. 1668 (2005), even if more conductive contact chemistry is used, such as carbenes on transition metals and on metal carbides, molecular-scale metal electrodes are extremely difficult to fabricate and lack specific chemistry for molecular attachment at their ends. This ill-defined bonding may result in unpredictable transport properties of electrons through the devices.

Carbon nanotubes provide new alternatives in molecular electronics research. Carbon nanotubes are a unique carbon-based molecular structure, consisting of graphitic layers wrapped to cylinders, usually having an extremely high length/width ratio. Carbon nanotubes can have multi-walls on their cylindrical shells, or only a single atomic layer. The latter is referred to as Single Wall Carbon Nanotubes ("SWNTs"), which have narrower diameters (typically in the range of 1~2 nm) and fewer defects on their molecular structure than their multi-walled counterparts. Depending on their chirality and diameters, SWNTs may be metallic or semiconducting. Due to their intriguing structure and unique electronic properties, SWNTs have become one of the most actively studied nanostructures in the past decade, and molecular electronic devices such as field effect transistors based on semiconducting SWNTs have been studied with increasing interest. For example, U.S. Patent Pub. No. 2004/0144972 to Dai et al., discloses a voltage controllable nanotube device where a gate electrode is capacitively coupled to a carbon nanotube via high-κ dielectric material.

The high aspect ratio of SWNTs makes them good candidates for constructing a molecular electronic device because metallic electrodes can be placed at a distance by traditional lithography methods. However, this benefit can also be a barrier for new generation nanometer-scale transistors. Reducing the width of active channels in these transistors is still a great challenge.

SWNTs have also been reported in sensing applications, such as high sensitivity gas detectors and glucose sensors. See S. Chopra et al., App. Phys. Lett. vol. 83, p. 2280 (2003); S. Chopra et al., App. Phys. Lett., vol. 80, p. 4632 (2002); P. W. Barone et al., Nat. Mat. vol. 4, p. 86 (2005). Physical affinity or chemical reactivity of SWNTs toward the molecules to be detected is the basis for these applications. However, since SWNTs have a large surface area and multitude of potential reaction centers, the specificity and sensitivity of the detection are still limited. Accordingly, a need remains for a technique for fabricating electronic devices from SWNTs with appropriate organic molecules.

SUMMARY OF THE INVENTION

The present invention provides techniques for precisely and/or functionally cutting single SWNTs, and selecting and/or synthesizing appropriate molecules as molecular wires to bridge the gap formed in the cut SWNTs.

In one embodiment, a transistor device is fabricated by forming a film of a novel contorted hexabenzocoronene on a base layer and depositing two or more electrodes on top of the film. The base layer preferably includes a primer layer formed on a substrate.

In another embodiment, a transistor device is fabricated by depositing two or more electrodes on a base layer and having one or more gaps between the electrodes; and filling the one or more gaps between the electrodes with one or more self-assembled single layers of a novel contorted hexabenzocoronene.

In another embodiment, a device to detect a target molecule is fabricated by obtaining a device of the present invention and attaching a molecule on the molecular bridge to detect the target molecule.

In yet another embodiment a molecular electronic device is fabricated by laying a SWNT on a base layer; depositing two or more electrodes on the SWNT; using a lithographic process to locally cut the SWNT between the electrodes to form a gap therein; and bridging the gap with a molecular wire.

In furtherance, this invention provides a method of precisely and/or functionally cutting single SWNTs and methods of selecting and/or synthesizing appropriate molecules as molecular wires to bridge the gap formed in the cut SWNTs.

In one embodiment, the cutting of a SWNT is achieved by opening a window of small width by lithography patterning of a protective layer on top of the SWNT, followed by applying an oxygen plasma to the exposed SWNT portion.

The gap of a cut SWNT may be reconnected by one or more difunctional molecules having appropriate lengths reacting to the functional groups on the cut SWNT ends to form covalent bonds.

In another embodiment, the gap of a cut SWNT is filled with a self-assembled monolayer from derivatives of contorted hexabenzocoranenes.

In yet another embodiment, a device based on molecular wire reconnecting a cut SWNT is used as a sensor to detect a biological binding event.

BRIEF DESCRIPTION OF THE DRAWINGS

The accompanying drawings, which are incorporated and constitute part of this disclosure, illustrate preferred embodiments of the invention and serve to explain the principles of the invention.

FIG. 19A is an illustration of a fluorenone compound 13 with a bis-alkoxyamine tether that can be used to react with a modified anti-FLAG antibody.

FIG. 19B is an illustration of binding and unbinding of the FLAG peptide sequence.

FIG. 19C is current-voltage curves showing the change in the ON-state resistance when the device of FIG. 19B binds and release the antigen.

Figure 1:
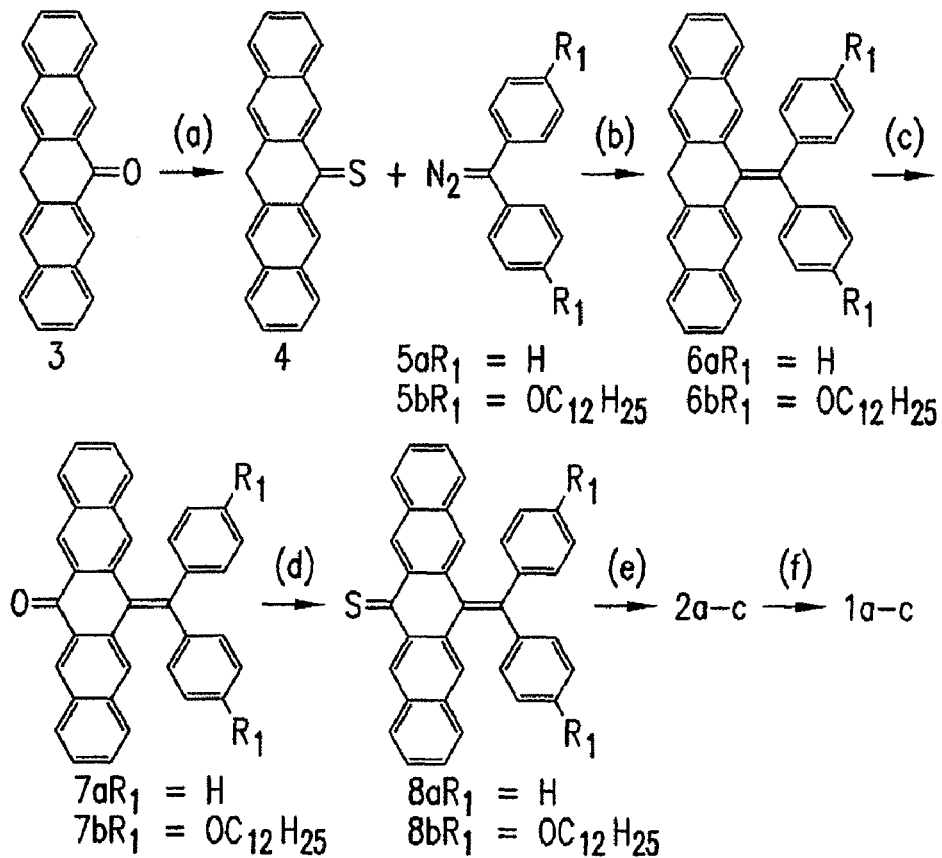
FIG. 1 is an illustration of the synthesis and chemical structure of a compound of formula 1, in accordance with an embodiment of the present invention.
Figure 1:
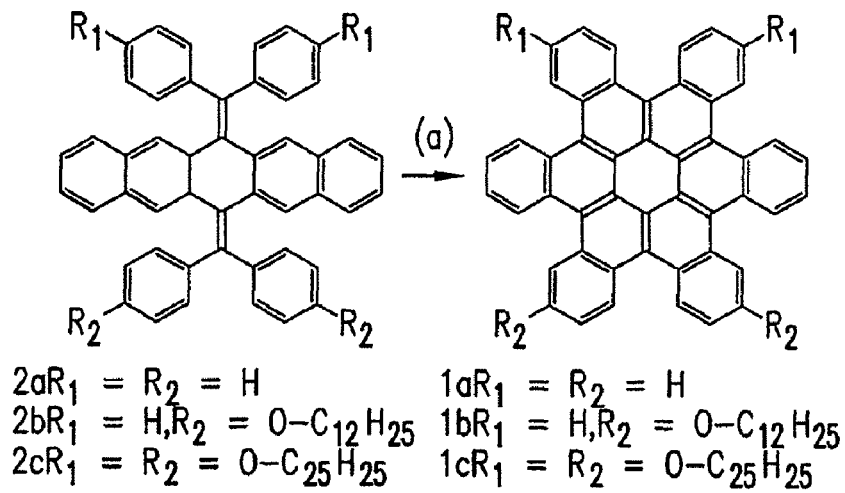

Throughout the drawings, the same reference numerals and characters, unless otherwise stated, are used to denote like features, elements, components or portions of the illustrated embodiments. Moreover, while the present invention will now be described in detail with reference to the Figs., it is done so in connection with the illustrative embodiments.

DETAILED DESCRIPTION OF THE INVENTION

The present invention provides techniques for fabricating devices by cutting SWNTs and forming transistors by inserting novel organic molecules and the devices fabricated in accordance with the methods. The devices may be used as small sized transistors in electronic paper, RFID tags, backplanes for OLED displays, low temperature replacement for amorphous silicon, among others. The present invention also provides techniques for constructing sensors based on such devices. The sensors may be used for a wide array of applications, for example, the detection of pH of a medium, a chemical substance, or a biological event.

The present invention provides for a method of fabricating transistor devices by forming a thin layer (or film) from appropriately selected molecules between metallic electrodes. To function as a molecular wire, the layer should contain long-range ordered structures to enable electron transport, e.g., a path of alternating single and double bonds to form a conjugated or substantially conjugated structure.

The general molecular formula of appropriate molecules, contorted hexabenzocoranenes 1, is shown in FIG. 1. $R_1$ and $R_2$ side groups in compound 1 may be same or different, and may have structures including oxylated linear alkyl chains or functional groups that are reactive toward appropriate surfaces to facilitate surface attachment, such as an acyl halide.

As used herein, the term "contorted hexabenzocoronene" refers to a new type of hexabenzocoronene or "HBC" whose aromatic core is distorted away from planarity by steric congestion in its proximal carbon atoms.

The terms "molecular wire" and "molecular bridge" are synonymous and refer to any molecule, in individual or aggregate form, that could be used to fill the gaps between two closely placed electrodes and function as a conducting means to complete an electric circuit.

The term "molecule" is well understood by those of skill in the art and encompasses single chemical molecules and biological macromolecules.

Figure 2:
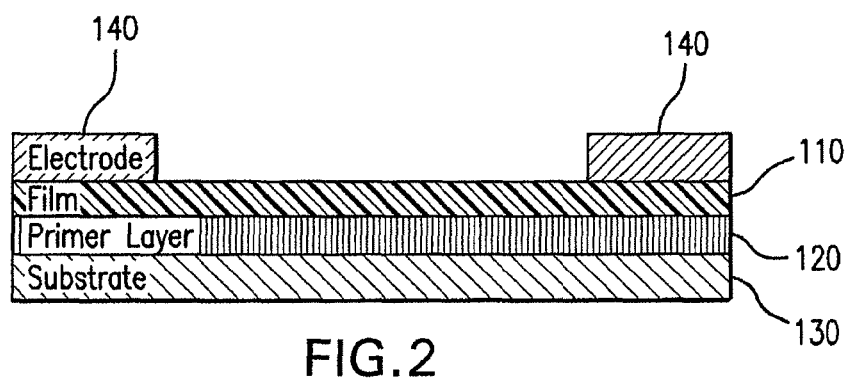
FIG. 2 is a schematic diagram illustrating a transistor device based on a spin-cast film of a compound of the formula 1 in accordance with an exemplary embodiment of the present invention.

Referring to FIG. 2, an exemplary transistor device is fabricated in accordance with an embodiment of the present invention as shown. A compound of the formula 1, where each R group is $O(CH_2)_nCH_3$ can be used to form a film 110.

A film 110 is formed as the surface of a primer layer 120, which in turn is laid on top of substrate 130. Metallic electrodes 140 are then deposited on top of the film.

As those skilled in the art will appreciate, any known techniques for depositing layers 110, 120 may be utilized. The film 110 may include one or more molecular layers of the compound. The primer layer 120 may be $SiO_2$, and the substrate 130 may be Si wafer. The spacing between electrodes is preferably less than 100 nm. Further, in a preferred embodiment, the electrodes are less than 10 nm wide.

Figure 3:
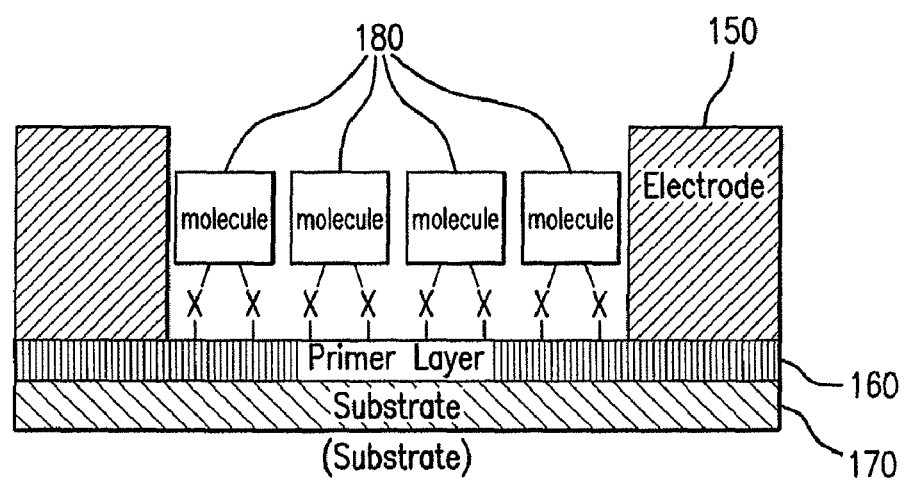
FIG. 3 is a schematic diagram illustrating a transistor device based on a self-assembled monolayer of a compound of the formula 1 in accordance with an exemplary embodiment of the present invention.

Referring next to FIG. 3, an alternative transistor device is fabricated in accordance with the present invention is shown. A compound of the formula 1, where $R_1$ may be H and/or $O(CH_2)_nCH_3$ and where $R_2$ is an acyl halide can be used to form self-assembled single-layer molecules 180. Metallic electrodes 150 are deposited on a primer layer 160, which, in turn, is laid on top of substrate 170. The gap between the electrodes is then filled with the self-assembled single-layer of molecules of the compound (180) which are immobilized to the primer layer by their surface attaching functional groups. Preferably, there are 10 or less molecules in the single-layer spaced about 1 nm apart, and the gap between the electrodes is about 5 nm.

Figure 4:
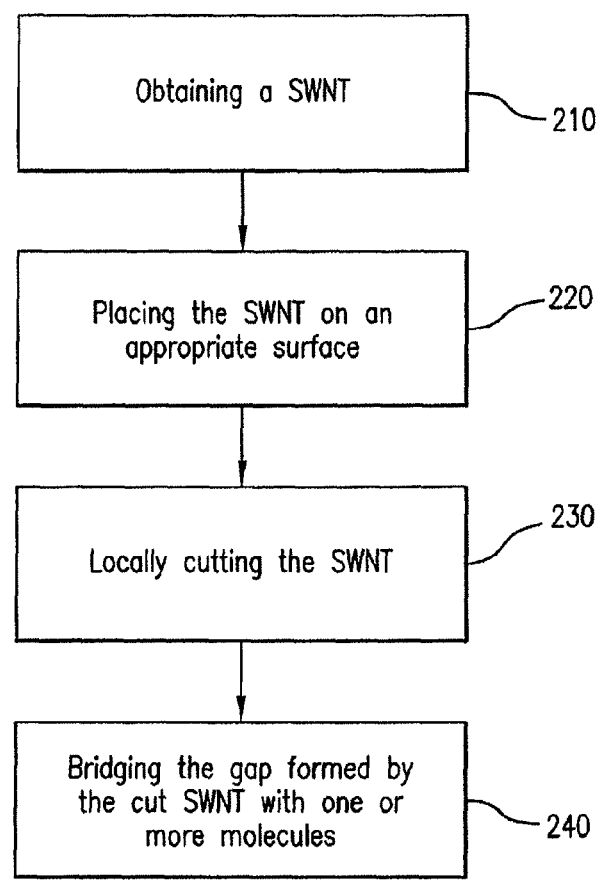
FIG. 4 is an illustration of a method of fabricating a cut-SWNT based device in accordance with an exemplary embodiment of the present invention.

Referring to FIG. 4, a method to create nanometer-scale molecular electronic devices based on SWNTs and molecular wires is shown. As shown in FIG. 4, the method includes obtaining a SWNT 210; placing the SWNT on a base layer 220; locally cutting the SWNT 230. Finally, the gap formed in the cut SWNT is filled with one or more molecules 240.

The devices fabricated in accordance with this method are characterized with ultrasmall active channels constituted by molecular wires, which can be manipulated and/or further functionalized for a variety of sensing applications, as discussed below.

Figure 5A:
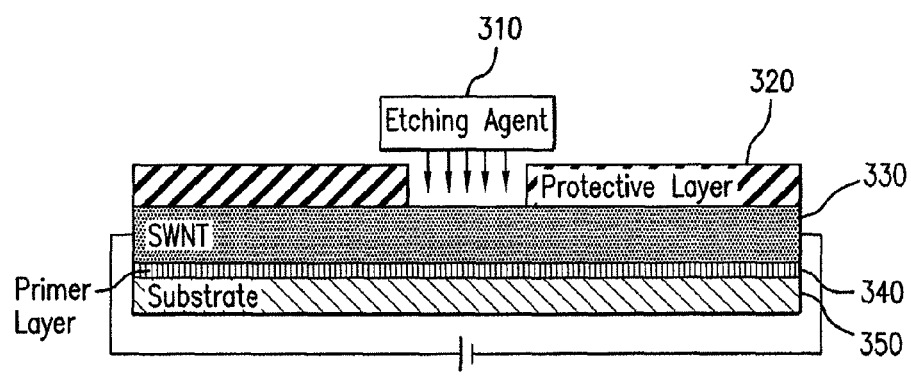
FIG. 5 is an illustration of a method for locally cutting a SWNT in accordance with an exemplary embodiment of the present invention.
Figure 5B:
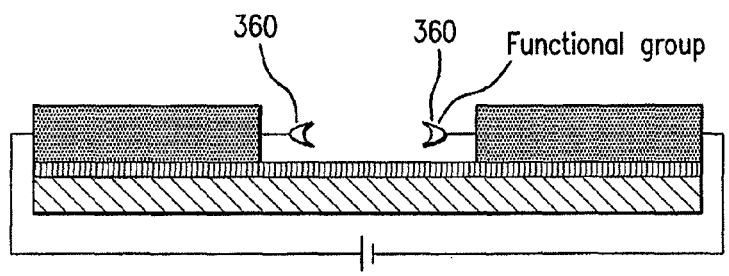

Cutting SWNTs can be accomplished using a localized chemical etching process. For example, referring to FIG. 5, an etching agent 310 is applied on a slit opened on a protective layer 320 coated on top of the SWNT 330 (which was laid upon a primer layer 340 and substrate layer 350), leaving two SWNT ends separated by a small gap and capped with the functional groups 360 resulting from this process. In a particular embodiment, the devices were put into TECH-NIQUES Series 800 RIE machine. The nanotubes were then locally cut through the open window by an oxygen plasma (50 W RF power, oxygen 250 mTorr, for 10 s). The protective layer may be formed by a polymer, e.g., polymethyl methacrylate ("PMMA"). The primer layer may be $SiO_2$, and the substrate layer may be a Si wafer.

Figure 6:
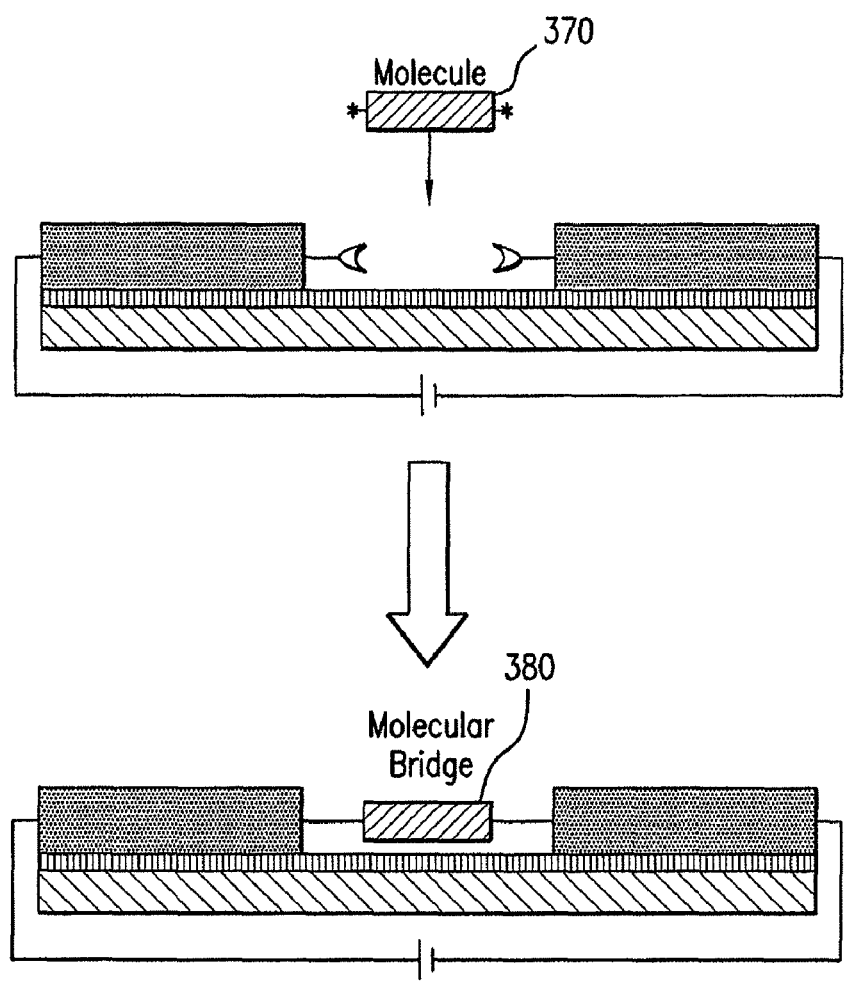
FIG. 6 is an illustration of a method for bridging the gap of a cut SWNT using a molecular bridge, in accordance with an exemplary embodiment of the present invention.
Figure 7:
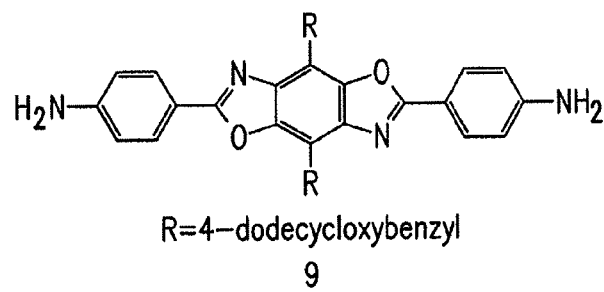
FIG. 7 is an illustration of exemplary structures of diamine compounds 9, 10, 11 and 12, in accordance with an embodiment of the present invention.
Figure 7:
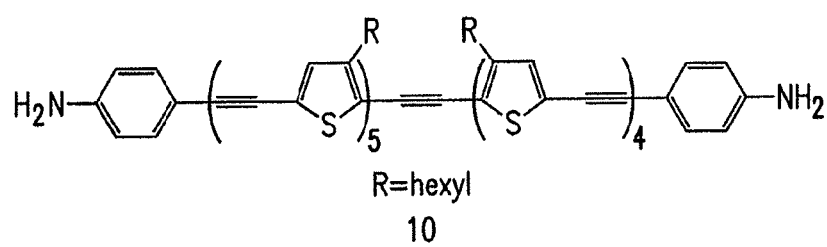
Figure 7:
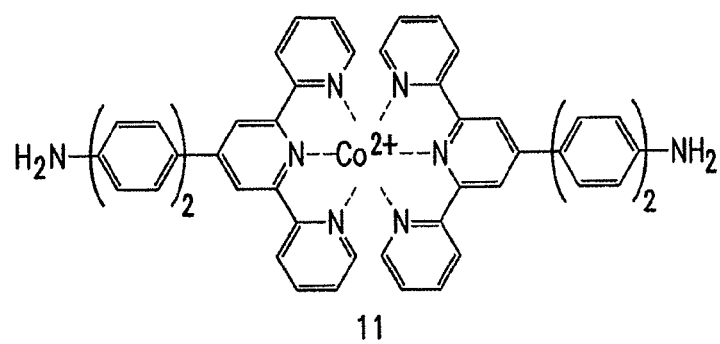
Figure 7:
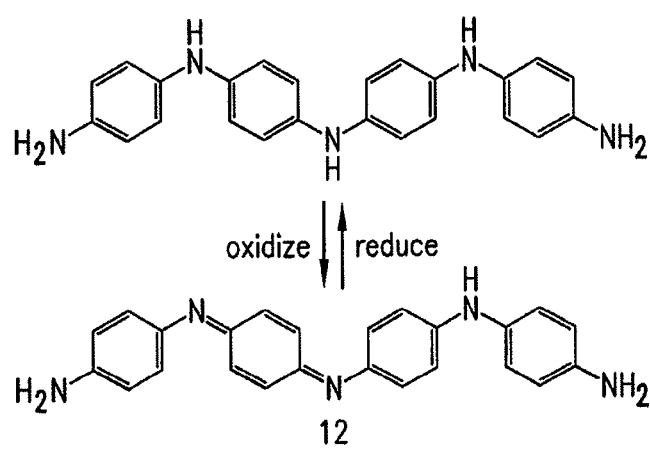

Bridging the cut SWNT ends may be accomplished in several ways. For example, molecules having appropriate functional groups 370 may be used to react to the functional groups at the cut SWNT ends to form a molecular bridge 380, as illustrated in FIG. 6. The bridging molecules may contain conjugation structure, i.e., alternating single and double bonds or a substantially conjugated structure having small breaks in the alternating single and double bonds, to facilitate electric current to flow through the circuit, and may be tailor made to have the appropriate size as well as functional groups at both ends. In one embodiment, compounds with at least two functional groups on either side, such as diamines of the formulas 9, 10, 11 and 12 illustrated in FIG. 7, are used to bridge a cut SWNT gap cut by an oxygen plasma. The resulting device including one or more molecular bridges spanning the gap of cut SWNT, each bridge including one individual diamine molecule connected to the cut SWNT through robust amide bonds at both ends.

An alternative way to bridge the cut SWNT ends is to use a film or self-assembled monolayer, where the constituent molecules are not necessarily chemically bonded to the cut SWNTs. The one-dimension nature of the contact of the molecular wire with SWNTs allows for various objectives, such as fabrication of high performance transistor devices and wide array of choices in controlling such devices by manipulating the monolayer structure.

Figure 8:
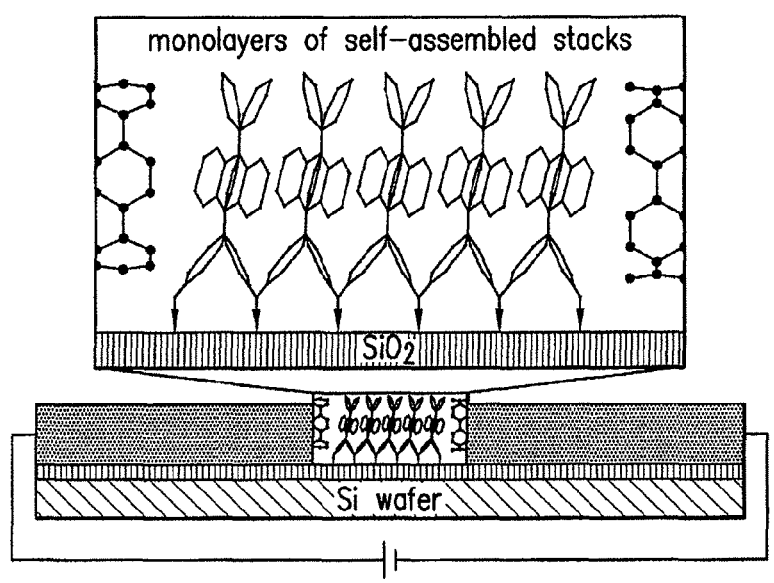
FIG. 8 is an illustration of a method for bridging the gap of a cut SWNT using a self-assembled monolayer, in accordance with an exemplary embodiment of the present invention.

In one embodiment, a transistor device is fabricated using a novel hexabenzocoronene compound 1 attached through the R-groups to a primer layer for assembly between the gap of a cut SWNT. FIG. 8 illustrates schematically a monolayer of self-assembled stacks formed by compound of the formula 1, wherein $R_1$ is —$O(CH_2)_nCH_3$ and $R_2$ is an acyl halide, probed with SWNT electrodes, wherein the primer layer may be $SiO_2$ and the substrate may be Si wafer.

In another embodiment, a transistor device is fabricated by dropping a compound of the formula 1 onto the gap of a cut SWNT so that it forms a film covering the gap but does not span the metallic electrodes. The compound does not necessarily form chemical bonds to the primer layer surface and does not need to contain surface reacting groups.

The electric characteristics of molecular devices formed by cut SWNTs and molecular bridge(s) are sensitive to local charge configuration near the molecular bridge. This high charge sensitivity can be exploited for detection of changes in the surrounding environment, such as a pH change in a medium, or the presence of a substance, such as a chemical compound.

The conductance of a molecular bridge can be influenced by pH of a medium to which the molecular bridge is exposed if the resonance structure of the molecular bridge can be altered by protonations and deprotonations. In one embodiment, a device based on a cut SWNT and polyaniline molecular bridge(s) is used to detect pH change in a medium.

The exposed active channel of the monolayer device shown in FIG. 6 can be employed for recognition of certain types of molecules that have strong affinity with the molecular stacks. In one embodiment, the device is used to detect an electron acceptor molecule by measuring the electric characteristic of the device; contacting the device with a substance containing the molecule and then measuring the electric characteristics of the device.

The above method may be used to detect various target molecules of π-electron acceptors that have strong affinity with the coronene structure shared by compounds of formula 1. For example, the target molecules may be electron deficient arenes that are used in explosives such as TNT.

Since many biological processes cause changes in the electrostatic environment of the molecular bridges, the devices based on cut SWNTs and molecular wires may be used as biosensors to detect nucleic acid hybridization, protein-protein interactions, and protein conformational changes with single-molecule sensitivity and at the single molecule/event level. This new level of sensitivity has not been previously possible with fluorescence-based techniques. These devices may have broad practical application in medical diagnostics (genomics and proteomics), drug discovery, environmental monitoring, and elsewhere.

Figure 9A:
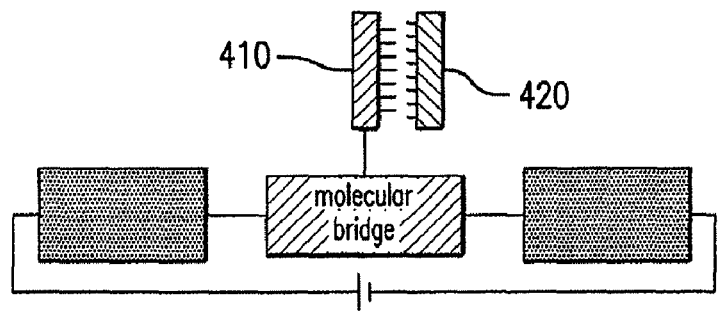
FIGS. 9A-C is an illustration of methods of fabricating and using cut SWNT based devices for sensing applications.
Figure 9B:
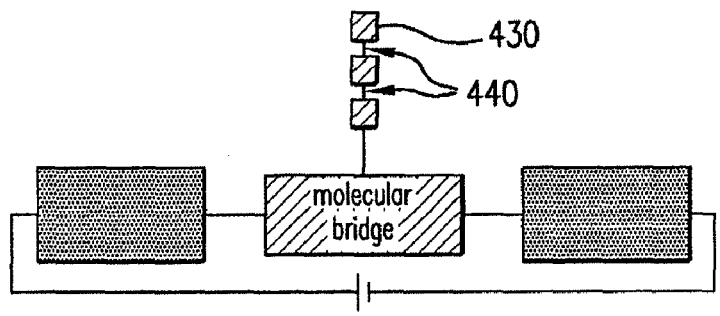
Figure 9C:
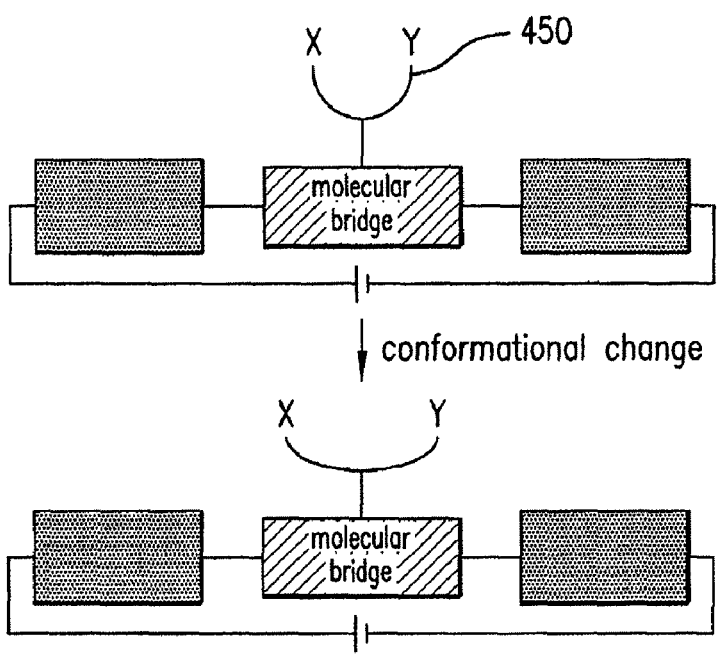

By way of example, FIG. 9 shows how the devices can be constructed for these sensing applications. In FIG. 9A, a molecule 410 (DNA, RNA, protein or an organic ligand) is attached on the molecular bridge to detect a target molecule 420 that can bind to it by physical association. For an attached DNA or RNA, the target molecule may be its complementary strand; for an attached protein, such as an antibody, the target molecule can be another protein or a smaller compound, such as an antigen. If an antibody capable of recognizing cancer cell tumor markers is attached, devices providing a biomedical diagnosis for tumor markers may be created. In FIG. 9B, possible locations (440) of breakdown of a protein, i.e., amie bonds or disulfide bridges, 430 catalyzed by an enzyme are detected. In FIG. 9C, a conformation change of a protein 450 induced by a small molecule or a change in the surrounding medium is detected.

A variety of chemical reactions can be employed to incorporate a second molecule into the molecular bridge for sensing applications illustrated above. In one embodiment, a fluorenone compound is used as the molecular bridge, and the fluorenone compound is further derivatized to incorporate a second molecule through oximation.

EXAMPLES

A number of Examples for practicing the present invention are provided below for illustration purpose only. In doing so, Applicants do not intend to limit the scope of the invention to the specific embodiments disclosed herein.

Example 1

Preparation of Contorted Hexabenzocoronenes

The syntheses for preparing contorted hexabenzocoronenes of formula 1 are schematically shown in FIG. 1. Ketone 3 was synthesized according to the well-known procedure disclosed in E. Clar, *Chemische Berichte* vol. 82, p. 495 (1949), the contents of which are incorporated by reference herein.

Synthesis of thioketone 4. Ketone 3 (4.4 g, 14.9 mmol) and Lawesson's reagent (0.7 eq, 4.2 g, 10.4 mmol) were added to 500 mL of toluene. The solution was heated to 80° C. for 2 hours. The dark green solution was allowed to cool to room temperature and 1200 mL of a 4:1 v/v mixture of hexanes and $CH_2Cl_2$ was added. Filtration through a plug of silica gel and a small amount of the same mixture of hexanes and $CH_2Cl_2$ was used to wash the remaining product from the silica gel. 3 was isolated as a green solid (2.2 g, 47%) after removal of the solvent and triturating with cold hexanes.

Synthesis of diphenyldiazomethane 5a: A mixture of 4,4'-dihydroxybenzophenone (21.4 g, 100 mmol), 1-bromododecane (49.8 g, 200 mmol), $K_2CO_3$ (50 g) in 500 mL of DMF were heated with stirring at 120° C. for 60 hours. After the mixture was cooled to room temperature, 1 L of water was added. The solution was extracted with $CH_2Cl_2$ (4×500 mL). The combined organic layers were dried with $MgSO_4$ and the most of the solvent removed under reduced pressure as a white solid formed. The solids were collected by filtration, washed with cold hexanes, and air dried to give 4,4'-didodecyloxybenzophenone (41.2 g, 75%). A mixture of 4,4'didodecyloxybenzophenone (20.6 g) and hydrazine monohydrate (20 mL) in 150 mL of pentanol were heated at reflux for 24 hours. After cooling to room temperature, a white solid precipitated which is collected by vacuum filtration, washed with 20 mL cold ethanol and air dried (19.4 g, 92%).

Synthesis of diaryldiazomethane 5b: To a mixture of compound 4,4'-didodecyloxybenzophenone hydrazone (10 g), yellow HgO (20 g) in 150 mL of THF, 0.5 mL saturated sodium hydroxide in ethanol was added. After stirring overnight the solution turned a dark purple color and the solution was filtered. The resulting solution was stored at −20° C. for future usage.

Synthesis of olefin 6a: 1.1 eq. of diphenyldiazomethane 5a dissolved in THF was added dropwise to a solution 1.0 g of thioketone 4 in 100 mL of THF. The diphenyldiazomethane was added until the green color of thioketone disappeared. After addition, the reaction was stirred for 1 hr. The thioepoxide was obtained by column chromatography ($SiO_2$, 3:1 hexanes:$CH_2Cl_2$, Rf=0.15) in quantitative yield (1.55 g, 100%). A solution of the thioepoxide (1.55 g, 0.35 mmol) was then heated at reflux with triphenylphosphine (1.01 g, 0.39 mmol) in 200 mL of anhydrous p-xylene for 12 hours. After cooling to room temperature, the solvent was removed under reduced pressure. The solid residue was dissolved in 200 mL of $CH_2Cl_2$ and concentrated under reduced pressure to 50 mL. Upon cooling on an ice/water bath, 6a precipitates from solution. The solids were isolated by vacuum filtration and washed with cold $CH_2Cl_2$. Compound 6a was isolated as a white solid (1.35 g, 92%).

Synthesis of olefin 6b: To 1.0 g of thioketone 4 dissolved in 100 mL of THF was added dropwise a solution of compound diaryldiazomethane 5b until the green color disappeared. The solution was stirred for 1 hr. The thioepoxide (1.79 g, 61% was obtained by column chromatography ($SiO_2$, 3:1 hexanes:$CH_2Cl_2$, Rf=0.15). A mixture of this thioepoxide (895 mg, 1.06 mmol) and triphenylphosphine (334 mg, 1.27 mmol) in 100 mL of p-xylene were heated at reflux for 12 hours. The solvent was removed under reduced pressure. Pure 6b (800 mg, 93%) was obtained after column chromatography as a white solid ($SiO_2$, 4:1 hexanes:$CH_2Cl_2$, Rf=0.20).

Synthesis of ketone 7a: $KMnO_4$ (460 mg, 2.91 mmol) was added as a solid to 6a (640 mg, 1.46 mmol) dissolved in 1 L of acetone. The solution was stirred for 2 hours at room temperature and then filtered. The solids were washed with 200 mL of $CH_2Cl_2$. The combined organic solutions were washed with 800 mL of water. The phases were separated and the aqueous phase was back extracted with $CH_2Cl_2$ (3×100 mL). Removal of the solvent followed by column chromatography ($SiO_2$, 45% $CH_2Cl_2$ in hexanes, Rf=0.20) provided pure 7a (380 mg, 56.7%). The first fraction from the column was unreacted starting material. ($SiO_2$, 20% $CH_2Cl_2$ in hexanes, Rf=0.20).

Synthesis of ketone 7b: Olefin 6b (250 mg, 0.31 mmol) was dissolved in 500 mL of acetone and added $KMnO_4$ (194 mg, 1.23 mmol). The mixture was stirred at room temperature for 2 hours. The solution was filtered using vacuum filtration and the solids washed with 200 mL of $CH_2Cl_2$. The organic washings were back washed with 800 mL of water. The aqueous washings were extracted with $CH_2Cl_2$ (3×100 mL). After removal of the volatiles, the ketone (150 mg, 59%) was purified using column chromatography ($SiO_2$, 40% $CH_2Cl_2$ in hexanes, Rf=0.20). The first fraction from the column was primarily starting material (20% $CH_2Cl_2$ in hexanes, Rf=0.20).

Synthesis of thioketone 8a. Ketone 7a (757 mg, 1.65 mmol) and Lawesson's reagent (368 mg, 0.91 mmol, 055 eq) were dissolved in 300 mL toluene. The solution was heated for 30 minutes at 80° C. After cooling to room temperature, the solution was filtered through a plug of silica gel and washed with 4:1 hexanes:$CH_2Cl_2$. The solvent was removed under reduced pressure to yield analytically pure compound 8a (774 mg, 1.63 mmol, 98%).

Synthesis of thioketone 8b: To 7b (147.4 mg, 0.178 mmol) in 80 mL toluene was added Lawesson's reagent (43.3 mg, 0.107 mmol). The solution was heated for 30 minutes at 80° C., and the reaction was monitored by TLC. After cooling to room temperature, the solution was filtered through a plug of silica gel and washed with 4:1 hexanes: $CH_2Cl_2$. The solvent was removed under reduced pressure to yield analytically pure compound 8b (150 mg, 98%).

Synthesis of bisolefin 2a: 1.1 eq. of diphenyldiazomethane 5a dissolved in THF was added dropwise to 8a (774 mg, 1.63 mmol) in 350 mL of THF. The diazomethane was added until the green color disappeared. The reaction was stirred at room temperature for 1 hr. The solvent was removed and the thioepoxide was purified by column chromatography ($SiO_2$, 3:1 $CH_2Cl_2$:hexanes, Rf=0.20) to yield 928 mg, 1.45 mmol, 88%. A solution of this thioepoxide (928 mg, 1.45 mmol) and triphenylphosphine (456 mg, 1.74 mmol) in 130 mL of anhydrous p-xylene was heated at reflux for 12 hours. The solvent was removed under reduced pressure. Recrystallization from 2:1 v/v methanol:$CH_2Cl_2$ provided pure 2a (859 mg, 98%).

Synthesis of bisolefin 2b: To thioketone 8a (327 mg, 0.69 mmol) in 350 mL of THF was added dropwise a THF solution of the diaryldiazomethane 5b until the green color disappeared. The reaction was stirred for an additional hour. The THF was removed under reduced pressure. The thioepoxide (600 mg, 0.60 mmol, 88%) was obtained by column chromatography ($SiO_2$, 3:1 $CH_2Cl_2$:hexanes, Rf=0.20). To this thioepoxide (600 mg, 0.60 mmol) in 100 mL of p-xylene was added triphenylphosphine (189 mg, 0.72 mmol). The mixture was heated at reflux for 10 hours. The solvent was removed under reduced pressure. Pure compound 2b (510 mg, 0.52 mmol, 87%) was obtained by column chromatography (4:1 $CH_2Cl_2$:hexanes, Rf=0.20).

Synthesis of bisolefin 2c: A THF solution of the diaryldiazomethane 5b was added to thioketone 8b (700 mg, 0.83 mmol) in 350 mL of THF until the green color disappeared. The solvent was removed under reduced pressure. The thioepoxide as obtained (928 mg, 0.67 mmol, 81%) by column chromatography ($SiO_2$, 3:1 $CH_2Cl_2$:hexanes, Rf=0.20). Pure compound 2c (859 mg, 98%) was obtained by column chromatography (4:1 $CH_2Cl_2$:hexanes, Rf=0.2). To this thioepoxide (928 mg, 1.45 mmol) in 130 mL of p-xylene was added triphenylphosphine (456 mg, 1.74 mmol). The mixture was heated at reflux for 12 hours. The solvent was removed under reduced pressure. Pure compound 2c (859 mg, 98%) was obtained by column chromatography (4:1 $CH_2Cl_2$:hexanes, Rf=0.20).

Synthesis of contorted hexabenzocoronenes 1a: The photolysis setup was performed in the well-known manner described in Liu, L; Yang B; Katz, T. J; Poindexter, M. K. *J. Org. Chem.* 1991, 56, 3769-3775, the contents of which are incorporated by reference herein. A mixture of compound 2a (500 mg, 0.82 mmol), iodine (965 mg, 3.78 mmol), propylene oxide (20 mL) in 350 mL of anhydrous benzene were irradiated with UV light (Hanovia 450 W high-pressure quartz Hg-vapor lamp) in an immersion well. Argon was bubbled through the reaction vessel during the photolysis. To maintain a constant temperature, the whole apparatus is submerged in a large bath of circulating water. After 12 hours of irradiation, the solvent is reduced to 15 mL under reduced pressure and a yellow powder precipitates. Compound 1a is isolated by vacuum filtration and washed with 100 mL of 20% $CH_2Cl_2$ in hexanes to yield 410 mg of 1a (83% yield).

Synthesis of contorted hexabenzocoronene 1b. A mixture of compound 2b (510 mg, 0.52 mmol), iodine (602 mg, 2.35 mmol), propylene oxide (10 mL) in 350 mL of anhydrous benzene were irradiated with UV light in an immersion well. Argon was bubbled through the reaction vessel during the photolysis. The whole apparatus was submerged in a large bath of circulating water. After 12 hours of irradiation, the solvent is reduced to 15 mL under reduced pressure and a yellow powder precipitates. Compound 1b is isolated by column chromatography ($SiO_2$, 4:1 hexanes:$CH_2Cl_2$, Rf=0.20).

Synthesis of contorted hexabenzocoronene 1c. A mixture of compound 2c (394 mg, 0.29 mmol), iodine (340 mg, 1.33 mmol), propylene oxide (20 mL) in 350 mL of anhydrous benzene were irradiated with UV light in an immersion well. Argon was bubbled through the reaction vessel during the photolysis. The whole apparatus was submerged in a large bath of circulating water. After 12 hours of irradiation, the solvent is removed under reduced pressure, and a yellow powder precipitates. Compound 1c is isolated by column chromatography ($SiO_2$, 4:1 hexanes:$CH_2Cl_2$, Rf=0.25).

Example 2

Preparation of a Transistor Device Based on Contorted HBCs

Figure 10A:
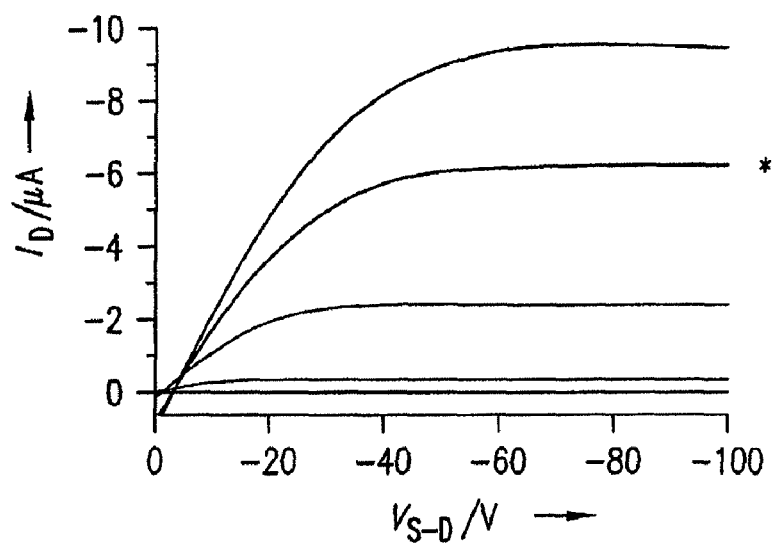
FIG. 10A is a graph of transconductance of an exemplary device in accordance with an embodiment of the present invention.

Compounds of the formula 1c were spin-cast from 1,2-dichloroethane or $CHCl_3$ to form uniform films (approximately 100-nm thick) on top of a $SiO_2$ substrate, and then Au was deposited as source and drain electrodes by thermal evaporation onto the spin-cast films through a metal-shadow mask. A transistor device thus obtained is illustrated schematically in FIG. 2. The transconductance and transistor output are shown in FIGS. 10A and 10B.

Figure 10B:
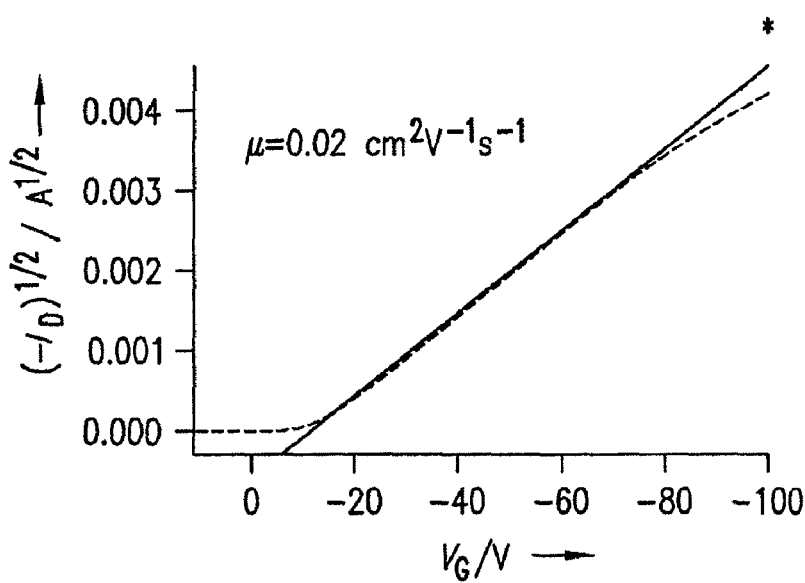
FIG. 10B is a graph of transistor output of an exemplary device in accordance with an embodiment of the present invention.

The mobility (0.02 $cm^2$ $V^{-1}s^{-1}$) shown in FIG. 10B is calculated from the linear portion of the data in FIG. 10B, and was based on a capacitance of 11.3 nF $cm^{-2}$ for the gate dielectric layer of 300 nm of $SiO_2$ and a monolayer of octadecyltrichlorosilane, obtained from a series of measurements over a range of frequencies. Other critical parameters, such as the threshold voltage for the device to turn on (as low as −3 V) and the on/off current ratios in the device (106:1), are also very good. These values are the best field-effect transistor properties achieved for a columnar discotic material.

Figure 11A:
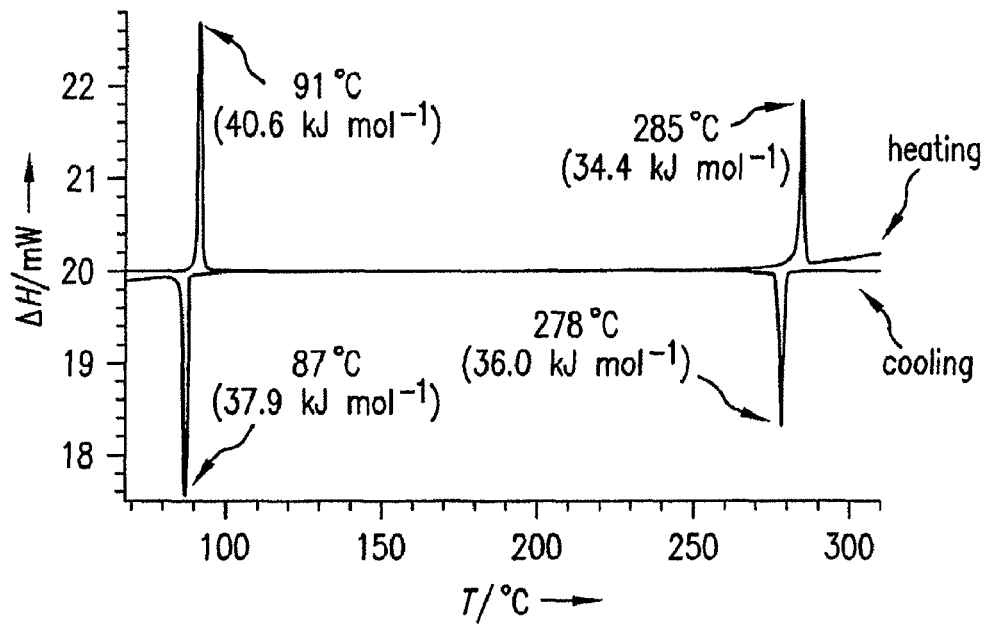
FIG. 11A is a DSC test result of a compound of the formula 1.

Several experimental techniques were used to determine the presence of mesophases in the spin-cast film by compound. A Differential Scanning Calorimetry (DSC) test showed an extra transition (at around 90° C.) other than the primary transition temperature (at around 280° C.), which indicated the presence of an intermediate phase. (See FIG. 11A).

Figure 11B:
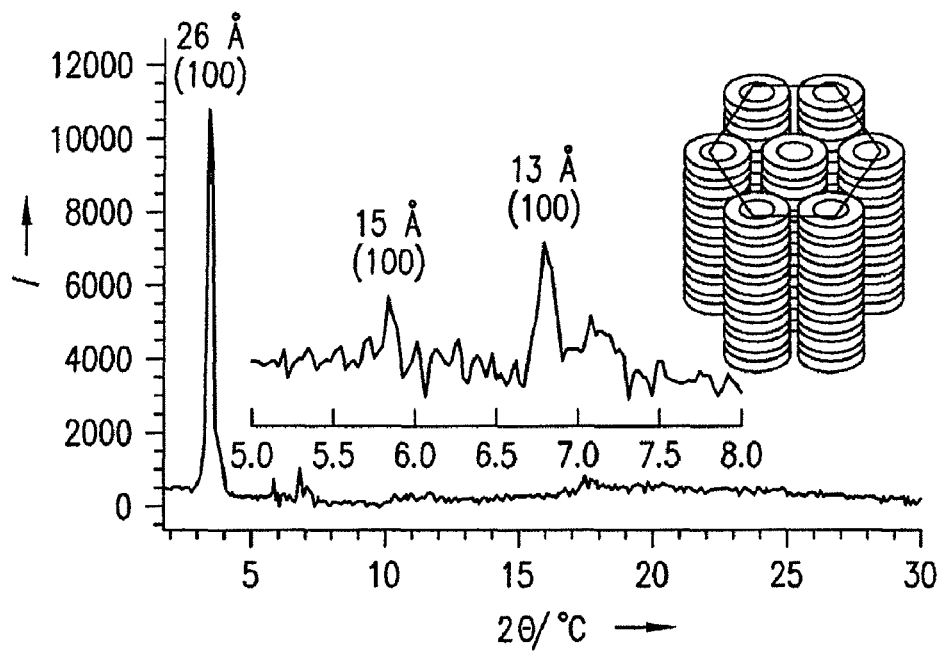
FIG. 11B is a X-ray diffraction result for a compound of the formula 1.

X-ray diffraction confirmed this intermediate phase. The compounds of the formula 1c were heated above 295° C. and cooled, and data were collected upon cooling to 120° C. in FIG. 11B. The diffractogram is dominated by an intense reflection characteristic of d=26 Å (d is the distance between neighboring lattice layers). The only other discernible features of the diffractogram are two very weak, higher-order reflections (d=15 Å and 13 Å) that are indexed to a hexagonal arrangement of columns. The lack of intensity in these higher-order reflections indicates that the columns are not well correlated with each other.

Figure 11C:
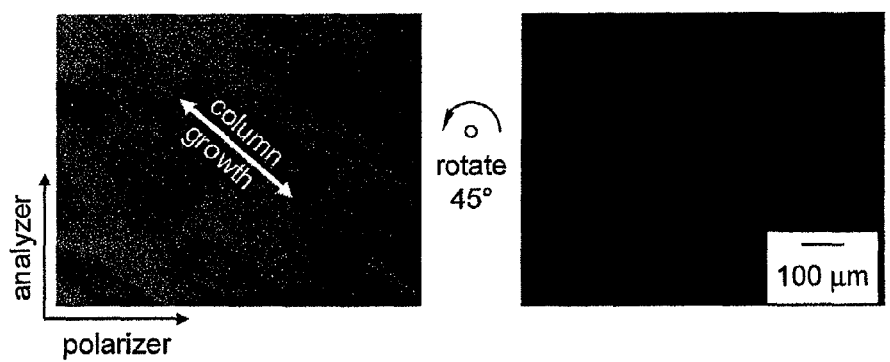
FIG. 11C is a polarized light microscopy for a compound of formula 1.
Figure 11D:
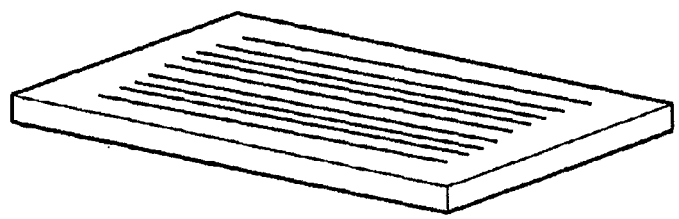
FIG. 11D is an illustration of ordered mesophase structure of a film formed by a compound of the formula 1.

Further, polarized light microscopy revealed that these columns in the mesophase aligned parallel to the surface. A sample film was cooled to just below 278° C. and captured as the mesophase formed is shown in FIG. 11C. The birefringence of the domains is extinguished when the column axes are aligned with the polarizer or analyzer and is maximally bright when the stage is rotated by 45°. The micrograph is characteristic of a planar arrangement of columns in a discotic mesophase shown schematically in FIG. 11D.

NMR, UV-Vis, and fluorescence spectroscopic techniques were also used to detect molecular association of the compound of formula 1c in solution. The results indicate the aggregation of this mesophase occurs in solution, and when a film is spin-cast onto a transparent substrate, birefringent domains form which have the same extinction as that described for the bulk film in FIG. 11C, suggesting that the film also has its columns aligned parallel to the substrate.

Example 3

Fabrication of a Cut SWNT-Film Transistor Device

Figure 15A:
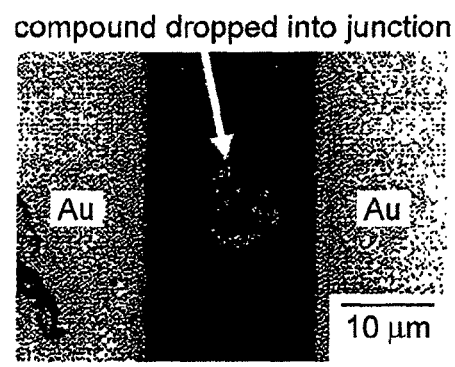
FIG. 15A is an illustration of a film of an exemplary compound of the formula 1 wherein each R group is O—$C_{12}H_{25}$ covering a cut SWNT gap, in accordance with an embodiment of the present invention.
Figure 15B:
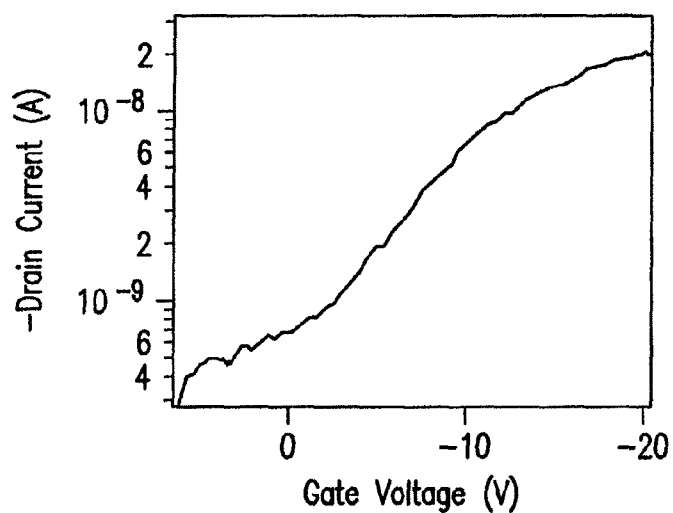
FIG. 15B is a plot for transfer characteristics of an exemplary device illustrated in FIG. 15A, in accordance with an embodiment of the present invention.

A compound of the formula 1c was spin cast onto the gap between a cut SWNT such that it covered gap of the cut SWNT but did not span the metal electrodes (shown in FIG. 15A). The device obtained shows p-type hole transporting semiconductor behavior (see FIG. 15B), but requires greater gate bias than a monolayer device where $R_2$ is COCl is used where surface attachment is effected.

Example 4

Preparation of SWNTs and Metallic Electrodes

Individual SWNTs were grown by chemical vapor deposition (CVD) using ethanol as the carbon source and CoMo-doped mesoporous $SiO_2$ catalyst particles patterned on thermally grown $SiO_2$ layer on top of degenerately doped silicon wafers. The SWNTs obtained were 1 to 2 nm in diameter.

Metallic electrodes (5 nm of Cr followed by 50 nm of Au) separated by ~20 μm were then deposited through a metal shadow mask onto the SWNTs using a thermal evaporator. The devices thus fabricated can be conveniently tested using the metal pads as source (S) and drain (D) contacts and the silicon substrate as a back gate (G).

Example 5

Cutting the SWNTs

A slit window with a width of less than 10 nm was first opened by ultrahigh-resolution electron-beam lithography on a spin-cast layer of polymethylmethacrylate (PMMA) coated on top of the SWNTs. Then an oxygen plasma (250 mTorr, 50 W RF power, 10 s exposure) was applied to the open window to locally cut the SWNT exposed. After development, the devices was washed by deionized water and dried with a stream of $N_2$ gas. The oxidation reaction resulted in a prevalence of carboxylic acid groups on the cut ends of the SWNTs.

Figure 12A:
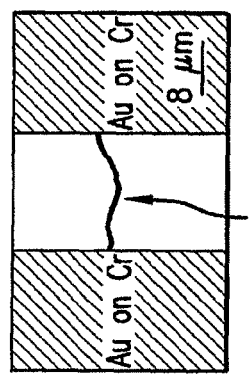
FIG. 12A is an exemplary scanning electron micrograph of a cut SWNT in accordance with an embodiment of the present invention.
Figure 12B:
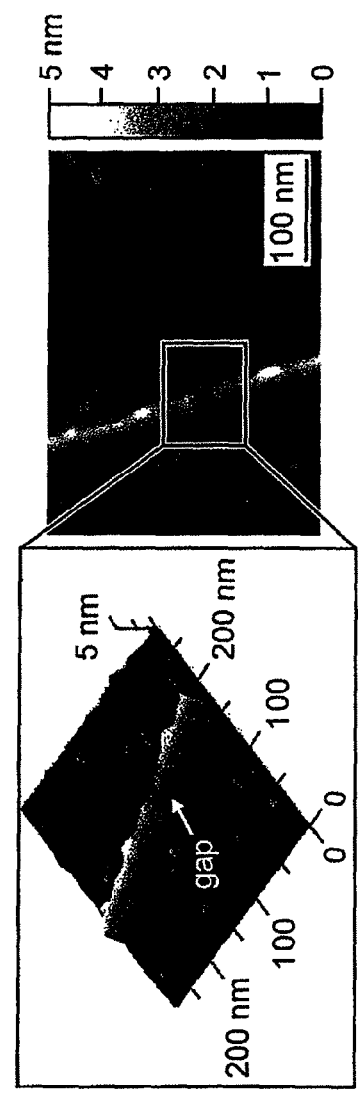
FIG. 12B is an Atomic Force Microscopy (AFM) micrograph of a cut SWNT in accordance with an embodiment of the present invention.
Figure 13A:
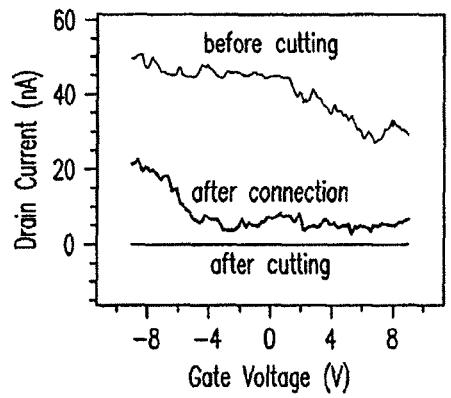
FIG. 13A is a I-$V_G$ plot for an exemplary device from a cut metallic SWNT connected with a compound of the formula 1 at source-drain voltage $V_{SD}$=50 mV, in accordance with an embodiment of the present invention.
Figure 13B:
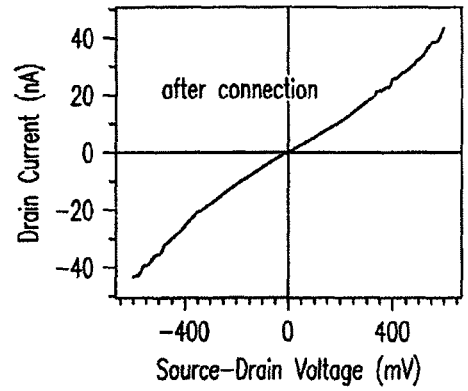
FIG. 13B is a I-$V_{SD}$ plot for the same device in FIG. 13A with no gate bias, in accordance with an embodiment of the present invention.
Figure 13C:
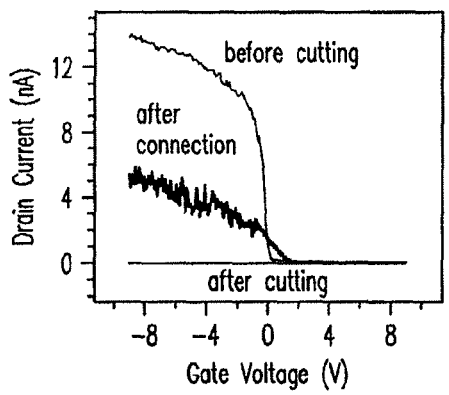
FIG. 13C is a I-$V_G$ plot at $V_{SD}$=50 mV for an exemplary device from a cut semiconducting SWNT connected with a compound of the formula 9, in accordance with an embodiment of the present invention.
Figure 13D:
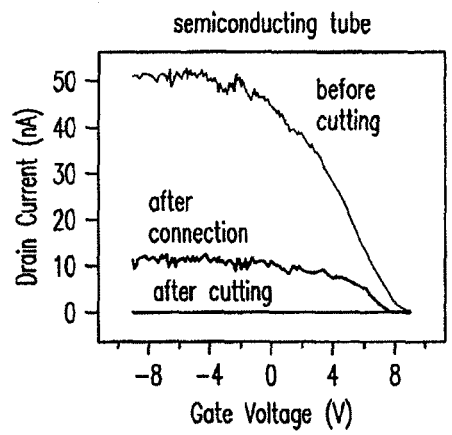
FIG. 13D is a I-$V_G$ plot at $V_{SD}$=50 mV for an exemplary device from a cut semiconducting SWNT connected with compound 12, in accordance with an embodiment of the present invention.
Figure 13E:
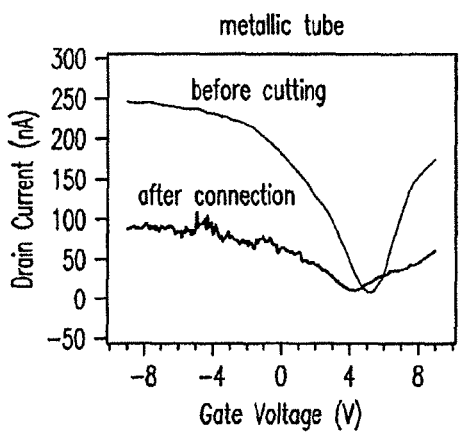
FIG. 13E is a I-$V_G$ plot at $V_{SD}$=50 mV for an exemplary device from a cut metallic SWNT connected with compound 11, in accordance with an embodiment of the present invention.

Under a scanning electron micrograph, the gaps obtained are too small to be observed. See FIG. 12A. However, Atomic Force Microscopy (AFM) can readily locate and image the gap, as shown in FIG. 12B, where the inset shows the height profile of the SWNT. The size of the gaps is estimated to be not exceeding 10 nm in diameter under the processing condition used above.

The electrical transport properties of the SWNT before and after oxidative etching were measured to determine the yield of completely cut tubes. Longer etch times give higher yields of the cutting but lower the yields of the chemical connection reactions. The etch time may be shortened so that the average gap can be narrower than the window opened in the PMMA layer. Under the processing conditions described above, ~20 to 25% of the tubes were completely cut among ~2500 devices tested.

Example 6

Bridging the Ends of a SWNT Gap with Molecular Wires

Please refer to the relevant portion of Supporting Online Material for: X. Guo et al., Science vol. 311, p. 356 (2006), for instructions on the synthesis of diamine compounds of formulas 9-12, which is incorporated herein by reference in its entirety.

The diamine compounds 9-12 shown in FIG. 7 were immersed (individually or in certain combinations) together with the SWNT devices obtained from Example 5 into a pyridine solution containing carbodiimide dehydrating/activating agent EDCI, as explained in A. Williams et al., Chem. Rev. vol. 81, p. 589 (1981), the contents of which are incorporated by referenced herein. The diamine end groups were chemically attached to the carboxylic acid by a dehydration reaction to form the amide linkage. After reaction, the devices were removed from the solution, rinsed with fresh solvent, dried, and then tested electrically.

These bridging molecular wires also allow for calibration of the etch process itself because the different species can be used as molecular rulers. For example, under optimized conditions, the yield for connection of compound 9 for more than 200 reactions is 10%. Using longer etch times, which give the larger gaps, reduces the yield of the coupling reaction with compound 9. Moreover, molecules of length similar to that of compound 9 give similar yields, implying that the yield is dominated by the statistics of having two functional groups appropriately spaced for bridging. Under identical conditions, the longer molecules (10 and 11) gave lower yields in their connection reactions (5%). A mixture of three oligomers based on compound 10 that ranged in length from 2 to 6 nm make the yield increase to 20%.

Electrical measurements on devices before cutting, after cutting, and after connection with compound 9 are shown in FIG. 13. FIG. 13A shows drain current (I) in the device made by metallic SWNT electrodes connected with compound 9 as a function of the gate voltage ($V_G$) at source-drain voltage $V_{SD}$=50 mV. FIG. 13B shows drain current as a function of $V_{SD}$ with no gate bias. FIG. 13C shows drain current as a function of $V_G$ at $V_{SD}$=50 mV for a semiconducting SWNT connected with compound 9. Before cutting, the device in FIGS. 13A and 13B shows metallic behavior, and the device in FIG. 13C shows typical p-type semiconducting behavior. After cutting, neither of the two devices show conductance (i.e., the conductance is at background noise level of the measurement (~2.0 pA). After molecular connection of the SWNT leads, the two devices recovered their original metallic or semiconducting behavior at reduced values of I, indicating that the gate modulates the nanotube conductance more strongly than that of the molecules. Similar I-$V_{SD}$ curves are obtained for measurements of other molecular bridges (compound 10 in FIG. 13D and compound 11 in FIG. 13E). The resistance of the molecular wires, or the molecular conductance, may be estimated from the drop in current after molecular connection.

Example 7

Fabrication of a Cut SWNT-Monolayer Device

The open SWNT circuits were immersed in a THF solution of a compound of the formula 1, wherein $R_1$ is H and $R_2$ is COCl and a compound of the formula 1, wherein $R_1$ is $OC_{12}H_{25}$ and $R_2$ is —COCl. The devices were removed from solution, rinsed, and dried under a stream of inert gas. UV-Vis spectroscopy, surface X-ray scattering, and florescence spectroscopy characterized the layer grown at the SWNT gaps as densely packed monolayers on silicon oxide on the surface of silicon wafers.

Figure 14A:
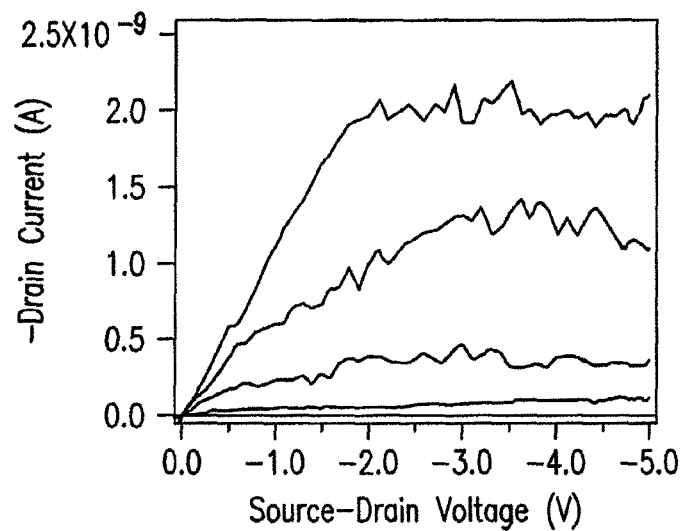
FIG. 14A is a plot for transistor output at $V_G$=0 to −5V in 1V steps for an exemplary device based on a monolayer of an exemplary compound of the formula 1, wherein $R_1$ is O—$C_{12}H_{25}$ and $R_2$ is COCl, and a cut SWNT, in accordance with an embodiment of the present invention.
Figure 14B:
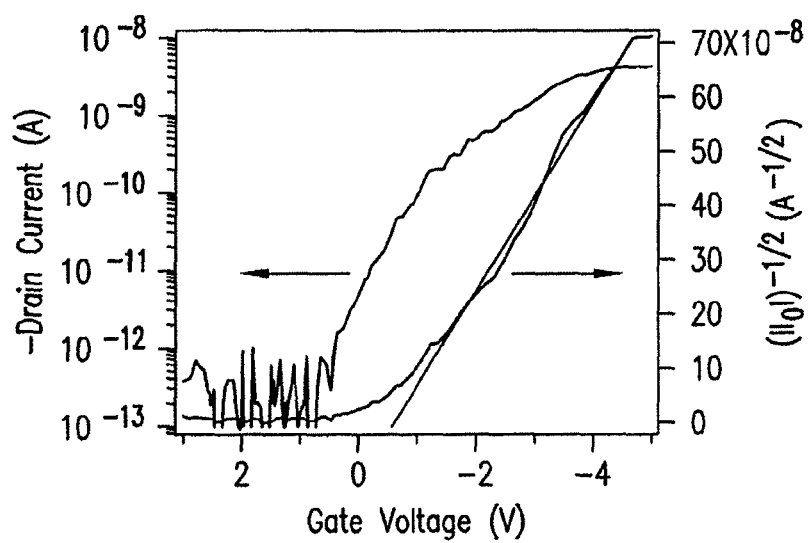
FIG. 14B is a plot for transfer characteristics for the same device in FIG. 14A at $V_D$=−2V, in accordance with an embodiment of the present invention.

Monolayers of both compounds behave as p-type semiconducting films. FIG. 14 shows the transistor characteristics for a monolayer of a compound of the formula 1, wherein $R_1$ is $OC_{12}H_{25}$ and $R_2$ is —COCl assembled in the same device characterized in FIG. 8. FIG. 14A shows the transistor output, $V_G$=0 to -5V in 1V steps (corresponding from bottom to top to the curves in FIG. 14A); FIG. 14B shows transfer characteristics for the same device at $V_D$=-2V. The ON/OFF current ratios of these devices are high (~5 orders of magnitude). This ratio is one of the critical parameters for the success of nanoscale organic field effect transistors and has proven difficult to optimize in ultrasmall organic Field Effect Transistors (FETs) with size smaller than 10 nm prepared with either metal or SWNT electrodes. The devices made with these contorted HBCs and SWNTs require much lower gate bias to switch (over an order of magnitude smaller compared to the gate bias required to switch other organic thin film materials).

Example 8

Detection of an Electron Rich Molecule

Figure 16A:
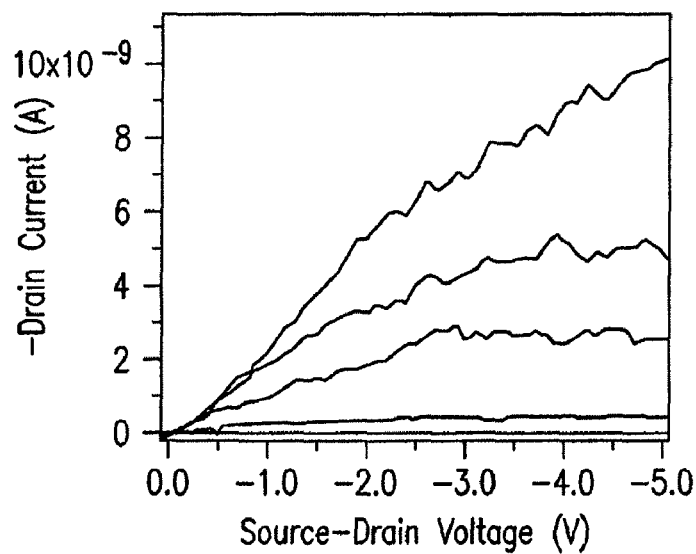
FIG. 16A is a plot for transistor output at $V_G$=0 to −5V in 1V steps for an exemplary device illustrated in FIG. 3 after being dipped in a TCNQ solution, according to an embodiment of the present invention.
Figure 16B:
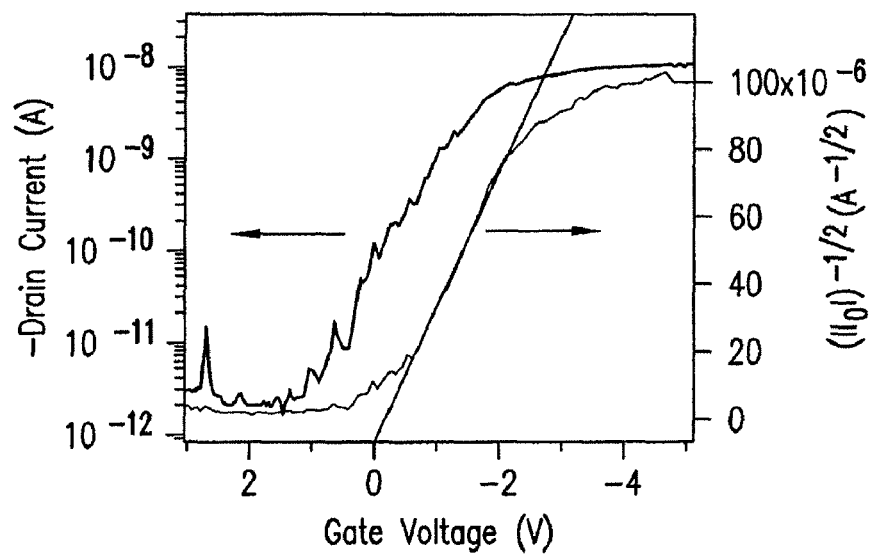
FIG. 16B is a plot for transfer characteristics at $V_D$=−2V for the TCNQ contacted device in FIG. 16A.

A device illustrated in FIG. 8, wherein the self-assembled monolayer of a compound of the formula 1, wherein $R_1$ is $OC_{12}H_{25}$ and $R_2$ is —COCl is used as the molecular wire, was dipped into a solution of an electron acceptor α,α,α',α'-tetracyano-p-quinodimethane (TCNQ). Electric characteristics of the device were measured both before and after the dipping. FIGS. 16A and 16B show that the transistor characteristics for the same device shown in FIGS. 14A and 14B where the monolayer is made by the compound. 10A plots the transistor output at $V_G$=0 to -5V in 1V steps; FIG. 16B plots the transfer characteristics for the device, $V_{SD}$=-2V. After contact with TCNQ, the OFF-current increases by roughly an order of magnitude and the ON-current increases slightly, and the threshold voltage shifts. An uncut metallic SWNT device shows no effect when dipped into a solution of TCNQ, indicating that the change observed in FIGS. 10A and 10B is due to the interaction of TCNQ with the self-assembled monolayer.

Example 9

Detection of pH Change in a Medium

Figure 17:
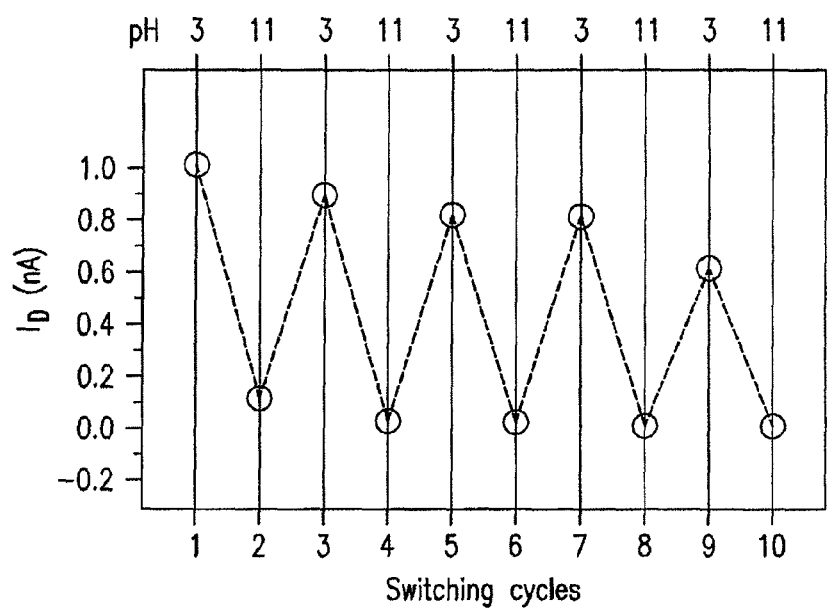
FIG. 17 is a plot for drain current of an exemplary device based on a cut SWNT bridged by compound 12 in response to pH change of a medium, according to an embodiment of the present invention.

A device fabricated according to FIG. 4 using compound 12 as the molecular bridge was subjected to a series of switching between a solution with pH 3 and a solution with pH=11. The current at saturation was monitored at the end of each cycle after the device was rinsed, dried, and tested. The response to changes in pH for the device is shown in FIG. 17. The molecular conductance varied significantly at different pH, i.e., nearly an order of magnitude, from ~5.2×10$^{-4}$ e$^2$/h at pH=3 to ~5.0×10$^{-5}$ e$^2$/h at pH=11 over many switching cycles.

Example 10

Detection of a Biological Binding Event

Figure 18A:
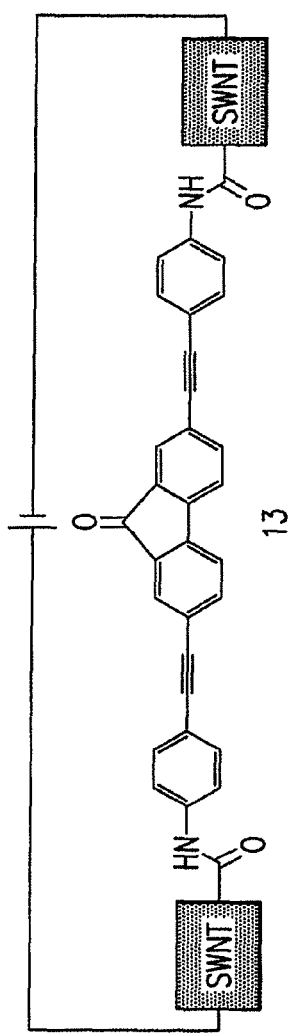
FIG. 18A is an illustration of an exemplary circuit based on a fluorenone bridge and a cut SWNT, according to an embodiment of the present invention.
Figure 18B:
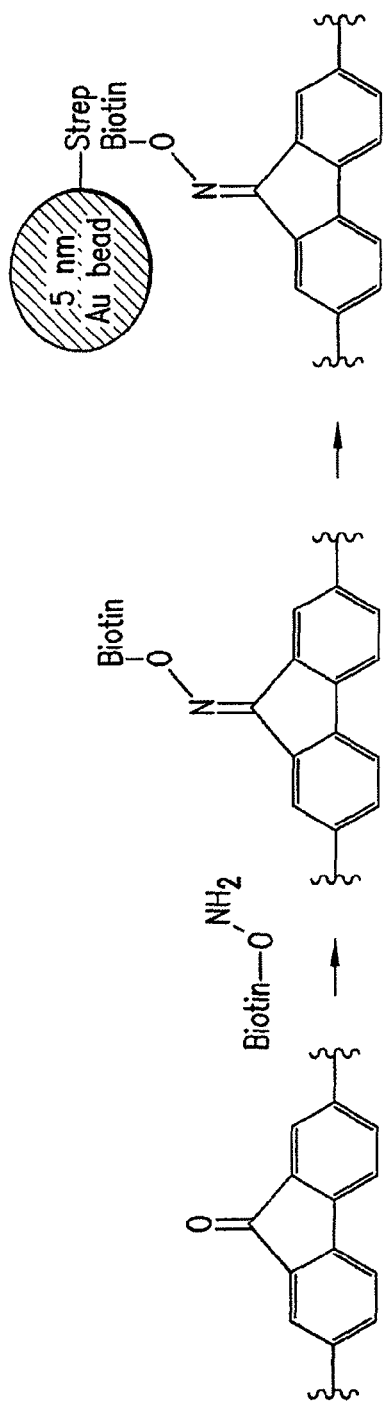
FIG. 18B is an illustration of a fluorenone compound 13 reacted to a functionalized Biotin to form an oxime, in accordance with an embodiment of the present invention.
Figure 18C:
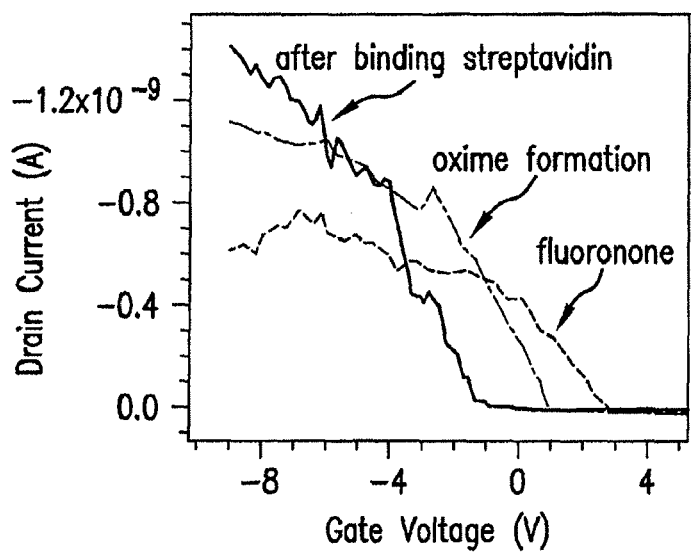
FIG. 18C is a plot for electric characteristics of an exemplary device after incorporation of the Biotin into the molecular bridge and after its association with Streptavidin, in accordance with an embodiment of the present invention.
Figure 18D:
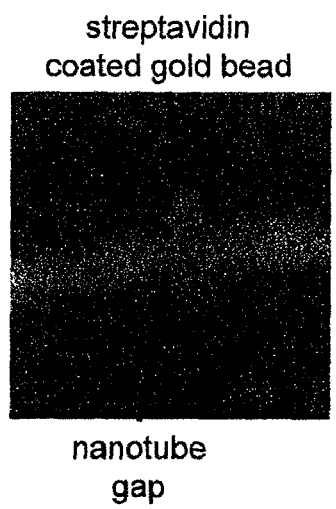
FIG. 18D is an AFM micrograph of an exemplary device in the gap area showing the gold label on the Streptavidin, in accordance with an embodiment of the present invention.

A device based on a cut SWNT and a molecular bridge of a compound of the formula 13, a fluorenone molecule was fabricated, whose structure is illustrated schematically in FIG. 18A. The fluorenone bridge was functionalized by Biotin (biotinylated alkoxyl amine) through an oxime formation, as illustrated in FIG. 18B. The device was then exposed to Streptavidin which is attached to a gold bead of diameter ~5 nm, and the electric characteristics before and after the exposure was measured. The strong affinity between Biotin and Streptavidin produced noticeable alterations of the electric characteristics of the device, as reflected in large shift in the threshold voltage and an increase in the low-field conductance shown in FIG. 18C. An AFM micrograph of the device in the SWNT gap area (FIG. 18D) shows the presence of the gold bead attached to the Streptavidin due to the Streptavidin-Biotin binding at the gap.

As another variation of detecting a biological binding event, a fluorenone bridge molecule 14 was utilized to attach an antibody to the bridge. In this case, the anti-FLAG antibody that was synthetically modified in the labs of Professor Matthew Francis from the Dept. of Chemistry at UC Berkeley was utilized. Before attachment the antibody was modified with a ketone. To attach this to the molecular bridge, a bis-alkxoylamine tether that was first reacted with the single molecule device 14 wired in between semiconducting SWNT leads to yield device 14A. As shown in FIG. 19, 14A presents an alkoxyl amine function for the sequestering of the modified antibody to yield 14B. We next tested the changes in conductance when the device is exposed to the FLAG peptide sequence to produce 14C. The antigen can then be removed from the device to return to 14B by incubation with the unattached anti-FLAG antibody. This cycle is shown schematically in FIG. 19. The preliminary data of FIG. 19C shows a factor-of-five change in the on-state conductance with antigen binding.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

The invention claimed is:

1. A method of fabricating a molecular electronic device, comprising:
   (a) disposing a SWNT on a base layer;
   (b) disposing two or more electrodes on the SWNT;
   (c) using a lithographic process to locally cut the SWNT between the electrodes to form a gap therein; and
   (d) disposing a molecular wire across the gap so that each end of the molecular wire contacts an electrode.

2. The method of claim 1, wherein the lithographic process comprises:
   (a) coating the SWNT with a protective layer having a slit therein; and
   (b) applying an etching agent to the SWNT through the slit.

3. The method of claim 2, wherein the protective layer comprises a polymer.

4. The method of claim 2, wherein the etching agent comprises an oxygen plasma.

5. The method of claim 1, wherein the molecular wire comprises a diamine compound having a length between the amine groups effective to bridge the gap.

6. The method of claim 5, wherein the diamine compound is selected from the group consisting of compounds of the formula 9, 10, 11, 12 and 13:

9

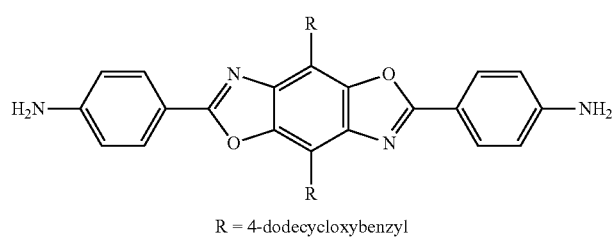

R = 4-dodecycloxybenzyl

10

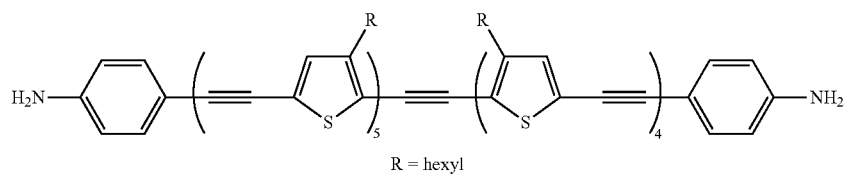

R = hexyl

11

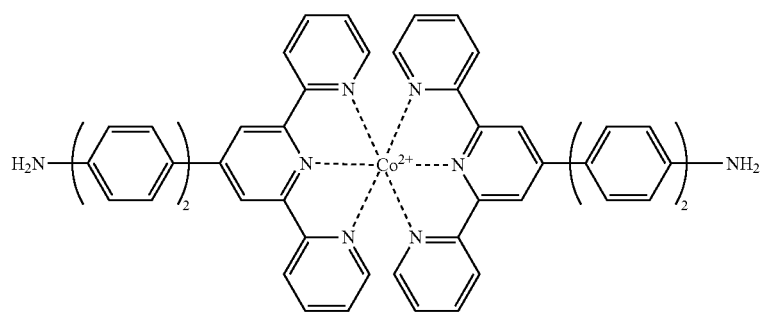

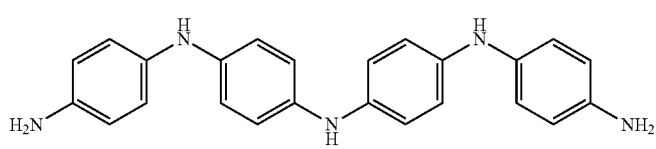

12

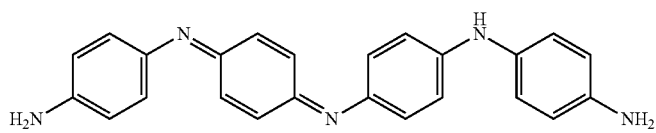

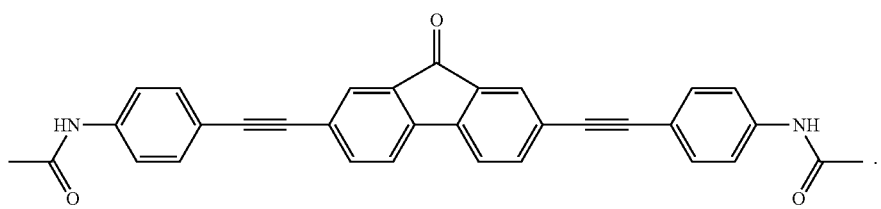

13

25

7. A method of fabricating a device to detect a target molecule, comprising:
(a) disposing a SWNT on a base layer;
(b) disposing two or more electrodes on the SWNT;
(c) using a lithographic process to locally cut the SWNT between the electrodes to form a gap therein; and
(d) disposing a molecular wire across the gap so that each end of the molecular wire contacts an electrode; and
(e) attaching a molecule on the molecular wire selected to detect the target molecule based on its affinity for attachment to the target molecule.

8. The method of claim 7, wherein the molecule is selected to detect a biological molecule.

9. The method of claim 8, wherein the biological molecule consists of an antigen.

10. The method of claim 8, wherein the biological molecule consists of streptavidin.

11. A molecular sensor comprising:
(a) a base layer having first and second sides;
(b) a SWNT cut into a first portion and a second portion, being disposed on the same side of the base layer such that a gap is formed between the first portion and the second portion of the cut SWNT;
(c) a first electrode disposed in contact with the first portion of the cut SWNT one side of the gap and a second electrode deposited in contact with the other side of the cut SWNT opposite the gap; and
(d) a molecular wire positioned in the cut SWNT gap and bridging the first portion to the second portion of the cut SWNT.

12. The sensor of claim 11, wherein the SWNT is cut using a lithographic process comprising:
(a) coating the SWNT with a protective layer having a slit therein; and
(b) applying an etching agent to the SWNT through the slit.

13. The sensor of claim 12, wherein the protective layer comprises a polymer.

14. The sensor of claim 12, wherein the etching agent comprises an oxygen plasma.

15. The sensor of claim 11, wherein the molecular wire comprises a diamine compound having two anime groups and having a length between the amine groups effective to bridge the gap.

16. The sensor of claim 15, wherein the diamine compound is selected from the group consisting of compounds of the formula 9, 10, 11, 12 and 13.

17. The sensor of claim 11, further comprising attaching a biological molecule on the molecular wire selected to detect the target molecule based on its affinity for attachment to the target molecule.

18. The sensor of claim 17, wherein the biological molecule is selected from the group consisting of an antibody and an aptamer.

19. The sensor of claim 17, wherein the biological molecule consists of biotin.

* * * * *